US008686130B2

(12) United States Patent (10) Patent No.: US 8,686,130 B2
Hirao et al. (45) Date of Patent: Apr. 1, 2014

(54) ARTIFICIAL FLUORESCENT BASES

(75) Inventors: Ichiro Hirao, Komae (JP); Michiko Hirao, Yokohama (JP); Shigeyuki Yokoyama, Yokohama (JP); Tsuneo Mitsui, Yokohama (JP)

(73) Assignees: Riken, Saitama (JP); Tagcyx Biotechnologies, Kanagawa (JP)

(*) Notice: Subject to any disclaimer, the term of this patent is extended or adjusted under 35 U.S.C. 154(b) by 82 days.

(21) Appl. No.: 13/500,303

(22) PCT Filed: Oct. 6, 2010

(86) PCT No.: PCT/JP2010/067989
§ 371 (c)(1),
(2), (4) Date: Apr. 4, 2012

(87) PCT Pub. No.: WO2011/043491
PCT Pub. Date: Apr. 14, 2011

(65) Prior Publication Data
US 2012/0245340 A1 Sep. 27, 2012

(30) Foreign Application Priority Data
Oct. 6, 2009 (JP) .................. 2009-232776

(51) Int. Cl.
*C07H 19/00* (2006.01)
*C07H 19/22* (2006.01)
(52) U.S. Cl.
USPC ............ 536/27.1; 536/27.11; 536/27.12; 536/27.13; 536/27.14; 536/27.2; 536/27.21
(58) Field of Classification Search
None
See application file for complete search history.

(56) References Cited

U.S. PATENT DOCUMENTS

| | | | |
|---|---|---|---|
| 5,438,131 A | 8/1995 | Bergstrom et al. | |
| 5,681,947 A | 10/1997 | Bergstrom et al. | |
| 5,780,233 A | 7/1998 | Guo et al. | |
| 6,451,530 B1 | 9/2002 | Hawkins | |

FOREIGN PATENT DOCUMENTS

| EP | 1921141 A1 | 5/2008 |
|---|---|---|
| WO | WO-2007/015557 A1 | 2/2007 |

OTHER PUBLICATIONS

"Derivative". (n.d.) The American Heritage® Dictionary of the English Language, Fourth Edition. (2003). Retrieved Aug. 21, 2013 from: http://www.thefreedictionary.com/derivative.*
Fujiwara et al. Bioorg. Med. Chem. Lett. (2001), vol. 11, pp. 2221-2223.*
Latorra et al. Molecular and Cellular Probes (2003), vol. 17, pp. 253-259.*
Extended European Search Report, dated Feb. 21, 2013, for European Application No. 10822158.1.
Kimoto, M., et al., "A New Unnatural Base Pair System between Fluorophore and Quencher Base Analogues for Nucleic Acid-Based Imaging Technology," J. Am. Chem. Soc., vol. 132, No. 43, 2010 (published on Web: Oct. 12, 2010), pp. 15418-15426.
Fujiwara, T., et al., "Synthesis of 6-(2-Thienyl)purine Nucleoside Derivatives That Form Unnatural Base Pairs with Pyridin-2-one Nucleosides," Bioorg. Chem. Lett., vol. 11, pp. 2221-2223, (2001).
Guo, Z., et al., "Enhanced discrimination of single nucleotide polymorphisms by artificial mismatch hybridization," Nature Biotechnology, vol. 15, pp. 331-335, (1997).
Hirao, I., et al., "An unnatural hydrophobic base pair system: site-specific incorporation of nucleotide analogs into DNA and RNA," Nature Methods, vol. 3, No. 9, pp. 729-735, (2006).
Hirao, I., et al., "A Two-Unnatural-Base-Pair System toward the Expansion of the Genetic Code," J. Am. Chem. Soc., vol. 126, pp. 13298-13305, (2004).
Hirao, I., et al., "An unnatural base pair for incorporating amino acid analogs into proteins," Nature Biotechnology, vol. 20, pp. 177-182, (2002).
Jean, J.M., et al., "2-Aminopurine fluorescence quenching and lifetimes: Role of base stacking," PNAS, vol. 98, No. 1, pp. 37-41, (2001).
Kimoto, M., et al., "Fluorescent probing for RNA molecules by an unnatural base-pair system," Nucleic Acids Research, vol. 35, No. 16, pp. 5360-5369, (2007).
Kimoto, M., et al., "A Unique Fluorescent Base Analogue for the Expansion of the Genetic Alphabet," J. Am. Chem. Soc., vol. 132, pp. 4988-4989, (2010).
Loakes, D., et al., "3-Nitropyrrole and 5-nitroindole as universal bases in primers for DNA sequencing and PCR," Nucleic Acids Research, vol. 23, No. 13, pp. 2361-2366, (1995).
Loakes, D., "The applications of universal DNA base analogues," Nucleic Acids Research, vol. 29, No. 12, pp. 2437-2447, (2001).
Loakes, D., et al., "5-Nitroindole as an universal base analogue," Nucleic Acids Research, vol. 22, No. 20, pp. 4039-4043, (1994).
Mitsui, T., et al., "Characterization of fluorescent, unnatural base pairs," Tetrahedron, vol. 63, pp. 3528-3537, (2007).
Mitsui, T., et al., "An Efficient Unnatural Base Pair for a Base-Pair-Expanded Transcription System," J. Am. Chem. Soc., vol. 127, pp. 8652-8658, (2005).
Nair, V., et al., "Arylation and Heteroarylation of Photochemically Generated Purinyl Radicals," J. Org. Chem., vol. 47, pp. 4526-4524, (1982).
Nichols, R., "A universal nucleoside for use at ambiguous sites in DNA primers," Nature, vol. 369, pp. 492-493, (1994).
Patel, N., et al., "Thermodynamics of interaction of a fluorescent DNA oligomer with the anti-tumour drug netropsin," Eur. J. Biochem., vol. 203, pp. 361-366, (1992).

(Continued)

*Primary Examiner* — Patrick Lewis
(74) *Attorney, Agent, or Firm* — Birch, Stewart, Kolasch & Birch, LLP

(57) ABSTRACT

The present invention relates to novel unnatural fluorescent nucleic acid bases, that is, a purine base, a 1-deazapurine base, and a 1,7-deazapurine base each having a functional group which consists of two or more heterocyclic moieties linked together, at the 6-position thereof (the 6-position of purine ring). The present invention also relates to a compound containing the unnatural base, a derivative thereof, and a nucleic acid containing a nucleotide having the unnatural base. The present invention also relates to a method of preparing the nucleic acid. The unnatural base of the present invention has excellent fluorescence characteristics and also has excellent properties as a universal base.

18 Claims, 10 Drawing Sheets

(56) References Cited

OTHER PUBLICATIONS

Rachofsky, E.L., et al., "Probing Structure and Dynamics of DNA with 2-Aminopurine: Effects of Local Environment on Fluorescence," Biochemistry, vol. 40, pp. 946-956, (2001).

Ward., D.C., et al., "Fluorescence Studies of Nucleotides and Polynucleotides," J. Biol. Chem., vol. 244, No. 5, pp. 1228-1237, (1969).

Watkins, N.E., et al., "Nearest-neighbor thermodynamics of deoxyinosine pairs in DNA duplexes," Nucleic Acids Research, vol. 33, No. 19, pp. 6258-6267, (2005).

Zhang, P., et al., "Exploratory studies on azole carboxamides as nucleobase analogs: thermal denaturation studies on oligodeoxyribonucleotide duplexes containing pyrrole-3-carboxamide," Nucleic Acids Research, vol. 26, No. 9, pp. 2208-2215, (1998).

* cited by examiner

Fig. 2
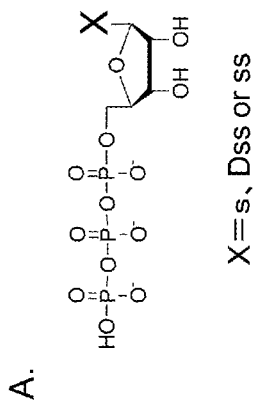
A.
X = s, Dss or ss
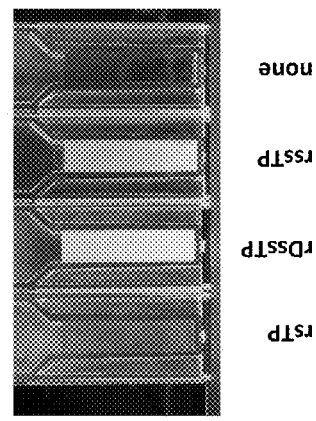
B. Fluorescence emission in cuvettes, irradiated with 365 nm UV transilluminator
rsTP  rDssTP  rssTP  none
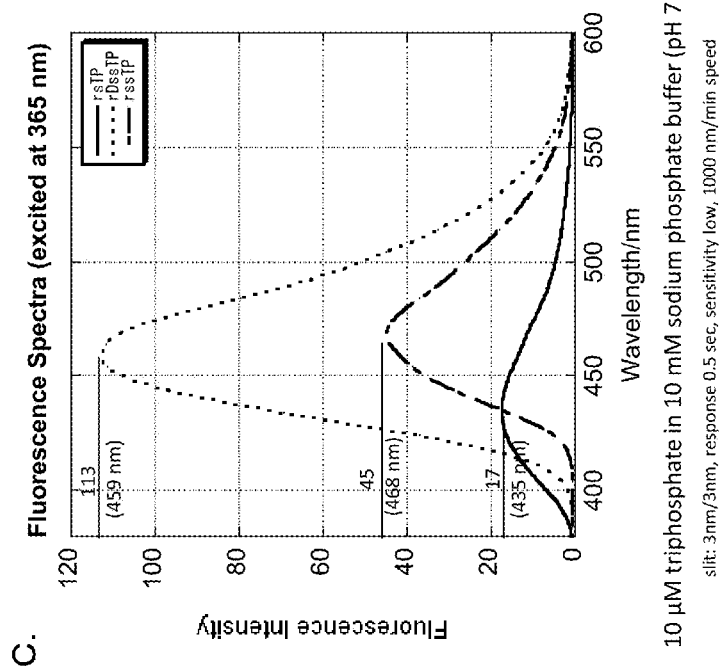
C.

A.

5'-³²P-ATAATACGACTCACTATAGGGAG-3'
3'-TATTATGCTGAGTGATATCCCTCGAAGAPaAGAGCT-5'
              +23          +28   +33

→ Klenow fragment (exo⁺) | dDssTP, 10 μM dTTP and dCTP

5'-³²P-ATAATACGACTCACTATAGGGAGGTTGADssTCTC-3'
3'-TATTATGCTGAGTGATATCCCTCGAAGAPaAGAGCT-5'

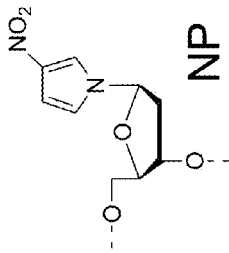

NP

5'-CGC-N$_1$-AATT-N$_2$-GCG-3'
3'-GCG-N$_2$-TTAA-N$_1$-CGC-5'

| N$_1$-N$_2$ | Tm (°C) |
|---|---|
| NP-A | 17.8 |
| NP-T | 19.3 |
| NP-G | 18.9 |
| NP-C | 23.2 |
| G-C | 68.9 |
| A-T | 64.4 |

Exploratory studies on azole carboxamides as nucleobase analogs: thermal denaturation studies on oligodeoxyribonucleotide duplexes containing pyrrole-3-carboxamide.
P. Zhang, W.T. Johnson, D. Klewer, N. Paul, Geoffrey Hoops, V.J. Davisson, and D.E. Bergstrom, Nucleic Acids Res., 26, 2208-2215 (1998).

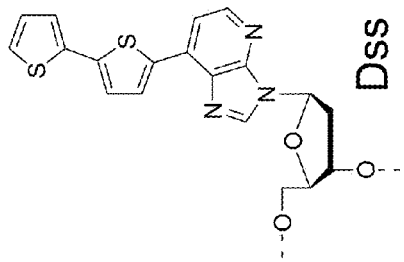

Dss

5'-GGTAAC-N$_1$-ATGCG-3'
3'-CCATTG-N$_2$-TACGC-5'

| N$_1$-N$_2$ | Tm (°C) |
|---|---|
| Dss-A | 45.3 |
| Dss-T | 43.9 |
| Dss-G | 45.9 |
| Dss-C | 44.9 |
| G-C | 53.1 |
| A-T | 48.6 |
| T-G | 42.4 |
| A-G | 38.6 |
| C-A | 33.6 |

SEQUENCE LISTING

```
<160> NUMBER OF SEQ ID NOS: 10

<210> SEQ ID NO 1
<211> LENGTH: 35
<212> TYPE: DNA
<213> ORGANISM: Artificial sequence
<220> FEATURE:
<223> OTHER INFORMATION: Template for DNA replication
<220> FEATURE:
<221> NAME/KEY: misc_feature
<222> LOCATION: (7)..(7)
<223> OTHER INFORMATION: n stands for pyrrolo-2-carbaldehyde (Pa)

<400> SEQUENCE: 1
tcgaganaga agctccctat agtgagtcgt attat                              35

<210> SEQ ID NO 2
<211> LENGTH: 23
<212> TYPE: DNA
<213> ORGANISM: Artificial sequence
<220> FEATURE:
<223> OTHER INFORMATION: Primer for DNA replication

<400> SEQUENCE: 2
ataatacgac tcactatagg gag                                           23
```

```
<210> SEQ ID NO 3
<211> LENGTH: 33
<212> TYPE: DNA
<213> ORGANISM: Artificial sequence
<220> FEATURE:
<223> OTHER INFORMATION: Replicated DNA
<220> FEATURE:
<221> NAME/KEY: misc_feature
<222> LOCATION: (29)..(29)
<223> OTHER INFORMATION: n stands for 7-(2,2'-bithiophene)imidazo[4,5-
      b]pyridine (Dss)

<400> SEQUENCE: 3
ataatacgac tcactatagg gaggttgant ctc                                  33

<210> SEQ ID NO 4
<211> LENGTH: 35
<212> TYPE: DNA
<213> ORGANISM: Artificial sequence
<220> FEATURE:
<223> OTHER INFORMATION: Template DNA for T7 transcription
<220> FEATURE:
<221> NAME/KEY: misc_feature
<222> LOCATION: (5)..(5)
<223> OTHER INFORMATION: n stands for cytidine or pyrrolo-2-carbaldehyde
      (Pa)

<400> SEQUENCE: 4
ctcanaggga agctccctat agtgagtcgt attat                                35

<210> SEQ ID NO 5
<211> LENGTH: 21
<212> TYPE: DNA
<213> ORGANISM: Artificial sequence
<220> FEATURE:
<223> OTHER INFORMATION: Primer for T7 transcription

<400> SEQUENCE: 5
ataatacgac tcactatagg g                                               21

<210> SEQ ID NO 6
<211> LENGTH: 17
<212> TYPE: RNA
<213> ORGANISM: Artificial sequence
<220> FEATURE:
<223> OTHER INFORMATION: Transcribed RNA
<220> FEATURE:
<221> NAME/KEY: misc_feature
<222> LOCATION: (13)..(13)
<223> OTHER INFORMATION: n stands for guanine, 7-(2.2'-bithiophene-5-
      yl)imidazo[4,5-b]pyridine (Dss), or 2-amino-6-(2,2'-bithiophene-5-
      yl)purine (ss)

<400> SEQUENCE: 6
gggagcuucc cunugag                                                    17

<210> SEQ ID NO 7
<211> LENGTH: 12
<212> TYPE: DNA
<213> ORGANISM: Artificial sequence
<220> FEATURE:
<223> OTHER INFORMATION: DNA for testing thermostability
<220> FEATURE:
<221> NAME/KEY: misc_feature
<222> LOCATION: (7)..(7)
<223> OTHER INFORMATION: n stands for any natural base or 7-(2,2'-
      bithiophene-5-yl)imidazo[4,5-b]pyridine (Dss)

<400> SEQUENCE: 7
ggtaacnatg cg                                                         12
```

```
<210> SEQ ID NO 8
<211> LENGTH: 12
<212> TYPE: DNA
<213> ORGANISM: Artificial sequence
<220> FEATURE:
<223> OTHER INFORMATION: DNA for testing thermostability
<220> FEATURE:
<221> NAME/KEY: misc_feature
<222> LOCATION: (6)..(6)
<223> OTHER INFORMATION: n stands for any natural base

<400> SEQUENCE: 8
cgcatngtta cc                                                           12

<210> SEQ ID NO 9
<211> LENGTH: 12
<212> TYPE: DNA
<213> ORGANISM: Artificial sequence
<220> FEATURE:
<223> OTHER INFORMATION: DNA for testing thermostability
<220> FEATURE:
<221> NAME/KEY: misc_feature
<222> LOCATION: (4)..(4)
<223> OTHER INFORMATION: n stands for adenine, guanine, or 3-
      nitropyrrole
<220> FEATURE:
<221> NAME/KEY: misc_feature
<222> LOCATION: (9)..(9)
<223> OTHER INFORMATION: n stands for any natural base

<400> SEQUENCE: 9
cgcnaattng cg                                                           12

<210> SEQ ID NO 10
<211> LENGTH: 52
<212> TYPE: RNA
<213> ORGANISM: Artificial sequence
<220> FEATURE:
<223> OTHER INFORMATION: shRNA targeted for firefly luciferase mRNA

<400> SEQUENCE: 10
ggagccuuca ggauuacaag auucaagagu cuuguaaucc ugaaggcucc uu               52
```

ARTIFICIAL FLUORESCENT BASES

This Application is the National Stage under 35 USC §371 of International Application Number PCT/JP2010/067989 filed on Oct. 6, 2010, which claims priority under 35 USC §119(a)-(d) of Application Number 2009-232776 filed in Japan on Oct. 6, 2009.

TECHNICAL FIELD

The present invention relates to a novel unnatural fluorescent nucleic acid base, i.e., a purine base, a 1-deazapurine base, or a 1,7-deazapurine base each having a functional group which consists of two or more heterocyclic moieties linked together, at the 6-position thereof (the 6-position of purine ring). The present invention also relates to a compound containing the unnatural base, a derivative thereof, and a nucleic acid containing a nucleotide having the unnatural base. The present invention also relates to a method of preparing the nucleic acid.

BACKGROUND ART

Fluorescent nucleic acid base analogs can be widely used in fluorescent labeling of nucleic acids. In the fluorescent labeling of nucleic acids, in general, a fluorescent dye is linked to any of natural bases, and this modified base is introduced into DNA or RNA by chemical synthesis or enzymatic reaction (replication or transcription). However, this method may inactivate the function of a nucleic acid by the fluorescent dye moiety, because it significantly protrudes from the structure of the nucleic acid and undergoes stacking with any base of the nucleic acid. In addition, the fluorescent dye is linked to a natural base; hence, such a base cannot be introduced into a specific position of a nucleic acid by replication or transcription. In contrast, the fluorescent nucleic acid base analog can label a nucleic acid while maintaining the structure and the function of the nucleic acid. Further, when the analog functions as an unnatural base pair in replication or transcription, it can be introduced at a specific position of DNA or RNA.

For example, 2-aminopurine and 2,6-diaminopurine are known as fluorescent nucleic acid base analogs (Patent Document 1 and Non-Patent Documents 1 to 4). The fluorescence intensities of these base analogs, however, are not so high. Further, when these base analogs are introduced into nucleic acids, the fluorescence of the analogs is quenched by stacking with neighboring bases. These base analogs are adenine (A) analogs and can be introduced into DNA or RNA by replication or transcription as complementary bases of tymine (T). However, the incorporation efficiencies of the adenine analogs are low, and they are introduced at positions corresponding to A of nucleic acids in replication or transcription and thus cannot be introduced at a specific position. If a nucleic acid has only one A, the base analog can be introduced at the position of the A; however, such a sequence of nucleic acid is a very particular case and thus lacks versatility. In addition, though these base analogs can substitute for A in DNA or RNA as analogs of A, substitution of such a base analog for another base (such as G, C, or T) may reduce the function of the nucleic acid.

The present inventors have intensively developed the third base pairs (unnatural base pairs) for expanding genetic information of DNA. The present inventors have successfully developed several unnatural base pairs that function in replication or transcription, such as an s-y base pair (s: 2-amino-6-thienylpurine, y: pyridin-2-one), a v-y base pair (v: 2-amino-6-thiazolyl purine), an s-Pa base pair (Pa: pyrrolo-2-carbaldehyde), a Ds-Pa base pair (Ds: 7-(2-thienyl)-imidazo[4,5-b]pyridine), and a Ds-Pn base pair (Pn: 2-nitropyrrole) (Non-Patent Documents 5 to 10). The unnatural bases s and v have fluorescence, and the inventors have also reported an analytical technique for local structure of nucleic acid using these unnatural bases. However, the fluorescence intensity of s is not so high, and s has a maximum excitation wavelength of 348 nm and a fluorescence wavelength of 435 nm; hence, a nucleic acid base analog having these wavelengths shifted to longer wavelengths is desired. Though v has a higher fluorescence intensity than s, it has low stability as a compound, which can be readily degraded under basic conditions. Its use is thus limited. With regard to the Ds-Pa base pair and the Ds-Pn base pair, DNA containing these unnatural base pairs can be amplified by PCR. Thus, these base pairs are very useful. However, the fluorescence of Ds by excitation at a wavelength of 350 nm or more is substantially invisible to the naked eye.

Accordingly, development of unnatural fluorescent bases that can be introduced into specific positions in DNA or RNA by replication or transcription will enable a novel method of fluorescent labeling of a nucleic acid to be established.

Incidentally, a base analog that forms a base pair with any natural base with substantially the same stability is called a universal base, and, for example, pyrrole-3-carboxamide, 3-nitropyrrole, and 5-nitroindole are known as such universal bases (Patent Documents 2 to 4 and Non-Patent Documents 11 to 17). However, there is a need for an unnatural base as a universal base having a higher thermal stability in the technical field of labeling a functional nucleic acid with an unnatural base.

CITATION LIST

Patent Documents

Patent Document 1: U.S. Pat. No. 6,451,530
Patent Document 2: U.S. Pat. No. 5,438,131
Patent Document 3: U.S. Pat. No. 5,681,947
Patent Document 4: U.S. Pat. No. 5,780,233

Non-Patent Documents

Non-Patent Document 1: J. M. Jean and K. B. Hall, Proc. Natl. Acad. Sci. USA, 98, 37-41 (2001)
Non-Patent Document 2: D. C. Ward, et al., J. Biol. Chem., 244, 1228-1237 (1969)
Non-Patent Document 3: N. Patel, et al., Eur. J. Biochem., 203, 361-366 (1992)
Non-Patent Document 4: E. L. Rachofsky, et al., Biochemistry, 40, 946-956 (2001)
Non-Patent Document 5: T. Mitsui, et al., Tetrahedron, 63, 3528-3537 (2007)
Non-Patent Document 6: M. Kimoto, et al., Nucleic Acids Res., 35, 5360-5369 (2007)
Non-Patent Document 7: I. Hirao, et al., Nature Methods, 3, 729-735 (2006)
Non-Patent Document 8: T. Mitsui, et al., J. Am. Chem. Soc., 127, 8652-8658 (2005)
Non-Patent Document 9: I. Hirao, et al., J. Am. Chem. Soc., 126, 13298-13305 (2004)
Non-Patent Document 10: I. Hirao, et al., Nature Biotechnology, 20, 177-182 (2002)
Non-Patent Document 11: P. Zhang, et al., Nucleic Acids Res., 26, 2208-2215 (1998)

Non-Patent Document 12: D. Loakes, et al., Nucleic Acids Res., 23, 2361-2366 (1995)

Non-Patent Document 13: D. Loakes, Nucleic Acids Res., 29, 2437-2447 (2001)

Non-Patent Document 14: N. E. Watkins and J. SantaLucia, Nucleic Acids Res., 33, 6258-6267 (2005)

Non-Patent Document 15: D. Loakes and D. M. Brown, Nucleic Acids Res., 22, 4039-4043 (1994)

Non-Patent Document 16: R. Nicols, et al., Nature, 369, 492-493 (1994)

Non-Patent Document 17: Z. Guo, et al., Nature Biotechnology, 15, 331-335 (1997)

SUMMARY OF INVENTION

Technical Problem

It is an object of the present invention to provide a novel unnatural fluorescent base.

In particular, it is an object of the present invention to provide a novel unnatural fluorescent base having at least one of the following properties:

1) It emits strong fluorescence;

2) It can be introduced into a specific position of DNA or RNA through replication or transcription by forming a base pair with an unnatural complementary base; and 3) It shows properties as a universal base.

Solution to Problem

The present inventors, who have diligently studied to solve the above-mentioned problems, have found that unnatural bases, that is, a purine base, 1-deazapurine, and 1,7-deazapurine each having a substituent which consists of two or more heterocyclic moieties linked together, at the 6-position thereof (the 6-position of purine ring) have excellent fluorescence characteristics and have arrived at the present invention.

The present inventors have developed the third base pairs (unnatural base pairs) functioning in replication or transcription, for expanding genetic information of DNA. At this time, the inventors developed unnatural fluorescent bases (such as ss: 2-amino-6-(2,2'-bithien-5-yl)purin-9-yl and Dss: 7-(2,2'-bithien-5-yl)imidazo[4,5-b]pyridin-3-yl) that can be site-specifically introduced into DNA or RNA by replication or transcription. The substrate for transcription of the unnatural base ss or Dss (ssTP or DssTP) complements an unnatural base Pa (pyrrolo-2-carbaldehyde) in template DNA and can be introduced into RNA by transcription. Furthermore, Dss can function as an unnatural base pair with Pa or Pn (2-nitropyrrole) in replication (for example, DNA containing a Dss-Pa or Dss-Pn base pair can be amplified by PCR). The inventors have also found that these unnatural fluorescent bases, Dss and ss, can form stable base pairs with any natural base in a double-stranded DNA to show properties as universal bases. As a result, the present inventors have arrived at the present invention.

For comprehension of the present invention, the background to the present invention has been described above. The scope of the present invention, however, should not be limited to the above description, but be defined by the attached claims.

The present invention provides the following embodiments 1 to 16.

Embodiment 1

A Compound Comprising an Unnatural Base Represented by Formula I

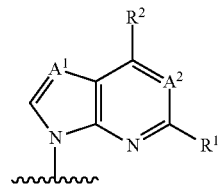

(I)

[wherein,
A$^1$ and A$^2$ each independently represent N or CH;
R$^1$ represents hydrogen or an amino group; and
R$^2$ represents a substituent selected from the group consisting of a 2,2'-bithien-5-yl group, a 2-(2-thiazolyl)thien-5-yl group, a 5-(2-thienyl)thiazol-2-yl group, and a 2,2',5',2"-terthien-5-yl group]
or a derivative thereof.

Embodiment 2

The Compound According to Embodiment 1, Represented by Formula II

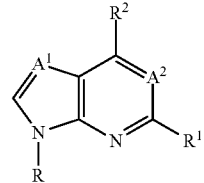

(II)

[wherein,
A$^1$ and A$^2$ each independently represent N or CH;
R is selected from the group consisting of hydrogen, a methyl group, carbohydrates, ribose, and deoxyribose;
R$^1$ represents hydrogen or an amino group; and
R$^2$ represents a substituent selected from the group consisting of a 2,2'-bithien-5-yl group, a 2-(2-thiazolyl)thien-5-yl group, a 5-(2-thienyl)thiazol-2-yl group, and a 2,2',5',2"-terthien-5-yl group].

Embodiment 3

The Compound According to Embodiment 1 or 2, Comprising a Group Selected from the Group Consisting of (i) a 7-(2,2'-bithien-5-yl)imidazo[4,5-b]pyridin-3-yl group (Dss);

(ii) a 7-(2,2',5',2"-terthien-5-yl)imidazo[4,5-b]pyridin-3-yl group (Dsss);

(iii) a 2-amino-6-(2,2'-bithien-5-yl)purin-9-yl group (ss);

(iv) a 2-amino-6-(2,2',5',2"-terthien-5-yl)purin-9-yl group (sss);

(v) a 4-(2,2'-bithien-5-yl)-pyrrolo[2,3-b]pyridin-1-yl group (Dsas);
(vi) a 4-[2-(2-thiazolyl)thien-5-yl]pyrrolo[2,3-b]pyridin-1-yl group (Dsav); and
(vii) a 4-[5-(2-thienyl)thiazol-2-yl]pyrrolo[2,3-b]pyridin-1-yl group (Dvas).

Embodiment 4

A Nucleoside or Nucleotide or a Derivative Thereof, Comprising an Unnatural Base Represented by Formula I

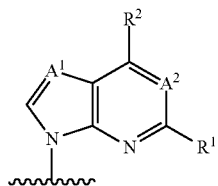

(I)

[wherein,
A$^1$ and A$^2$ each independently represent N or CH;
R$^1$ represents hydrogen or an amino group; and
R$^2$ represents a substituent selected from the group consisting of a 2,2'-bithien-5-yl group, a 2-(2-thiazolyl)thien-5-yl group, a 5-(2-thienyl)thiazol-2-yl group, and a 2,2',5',2''-terthien-5-yl group].

Embodiment 5

The Nucleoside or Nucleotide or the Derivative Thereof According to Embodiment 4, Wherein the Unnatural Base Represented by Formula I is Selected from the Group Consisting of (i) a 7-(2,2'-bithien-5-yl)imidazo[4,5-b]pyridin-3-yl group (Dss);
(ii) a 7-(2,2',5',2''-terthien-5-yl)imidazo[4,5-b]pyridin-3-yl group (Dsss);
(iii) a 2-amino-6-(2,2'-bithien-5-yl)purin-9-yl group (ss);
(iv) a 2-amino-6-(2,2',5',2''-terthien-5-yl)purin-9-yl group (sss);
(v) a 4-(2,2'-bithien-5-yl)-pyrrolo[2,3-b]pyridin-1-yl group (Dsas);
(vi) a 4-[2-(2-thiazolyl)thien-5-yl]pyrrolo[2,3-b]pyridin-1-yl group (Dsav); and
(vii) a 445-(2-thienyl)thiazol-2-yl]pyrrolo[2,3-b]pyridin-1-yl group (Dvas).

Embodiment 6

The nucleoside or nucleotide or the derivative thereof according to Embodiment 4 or 5, wherein the nucleoside or the nucleotide comprises β-D-ribofuranosyl or 2-deoxy-β-D-ribofuranosyl as a carbohydrate moiety.

Embodiment 7

The nucleoside or nucleotide or the derivative thereof according to any one of Embodiments 4 to 6, wherein the nucleotide is deoxyribonucleo side 5'-triphosphate or ribonucleoside 5'-triphosphate.

Embodiment 8

The nucleoside or nucleotide or the derivative thereof according to any one of Embodiments 4 to 6, being a phosphoramidite derivative.

Embodiment 9

The nucleoside or nucleotide or the derivative thereof according to any one of Embodiments 4 to 6, emitting fluorescence by excitation at a wavelength of 200 nm or more.

Embodiment 10

The nucleoside or nucleotide or the derivative thereof according to any one of Embodiments 4 to 6, being used as a universal base.

Embodiment 11

A nucleic acid containing a nucleotide according to any one of Embodiments 4 to 6.

Embodiment 12

The nucleic acid according to Embodiment 11, emitting fluorescence by excitation at a wavelength of 200 nm or more.

Embodiment 13

The nucleic acid according to Embodiment 11 or 12, being a functional nucleic acid selected from the group consisting of antisense DNAs, antisense RNAs, ribozymes, deoxyribozymes, RNA interference-inducing nucleic acids such as siRNAs and shRNAs, microRNAs, antimicroRNA nucleic acid molecules, decoy nucleic acids, DNA aptamers, and RNA aptamers.

Embodiment 14

A nucleic acid mimic comprising:
a base moiety comprising an unnatural base represented by Formula I:

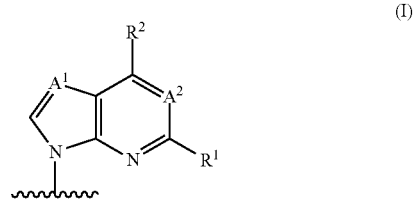

(I)

[wherein,
A$^1$ and A$^2$ each independently represent N or CH;
R$^1$ represents hydrogen or an amino group; and R² represents a substituent selected from the group consisting of a 2,2'-bithien-5-yl group, a 2-(2-thiazolyl)thien-5-yl group, a 5-(2-thienyl)thiazol-2-yl group, and a 2,2',5',2''-terthien-5-yl group]

or a derivative thereof; and a backbone moiety being a nucleic acid mimic backbone selected from the group consisting of morpholino-nucleotides, locked nucleic acids (LNAs), and peptide nucleic acids (PNAs).

Embodiment 15

A Method of Introducing an Unnatural Base Represented by Formula I

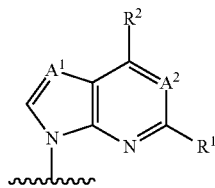
(I)

[wherein,
A¹ and A² each independently represent N or CH;
R¹ represents hydrogen or an amino group; and
R² represents a substituent selected from the group consisting of a 2,2'-bithien-5-yl group, a 2-(2-thiazolyl)thien-5-yl group, a 5-(2-thienyl)thiazol-2-yl group, and a 2,2',5',2''-terthien-5-yl group]

or a derivative thereof into DNA or RNA by replication of a nucleic acid, wherein said method comprises:

using a template strand which is a nucleic acid containing a nucleotide having a base (hereinafter referred to as Pa derivative) represented by Formula III:

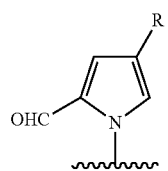
(III)

[wherein,
R is selected from the group consisting of hydrogen and substituted or unsubstituted alkyl, alkenyl, and alkynyl groups, wherein
the substituent of the substituted alkyl, alkenyl, or alkynyl group is a functional group or a fluorescent functional group];

conducting replication, transcription, or reverse transcription of a nucleic acid by using deoxyribonucleoside 5'-triphosphate or ribonucleoside 5'-triphosphate having an unnatural base represented by Formula I as a replication substrate; and thereby a nucleic acid containing a base pair of the base Pa derivative and the unnatural base represented by Formula II is generated and a nucleotide having the unnatural base represented by Formula II is introduced into DNA or RNA.

Embodiment 16

A Method of Introducing an Unnatural Base Represented by Formula I

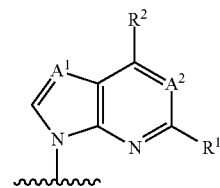
(I)

[wherein,
A¹ and A² each independently represent N or CH;
R¹ represents hydrogen or an amino group; and
R² represents a substituent selected from the group consisting of a 2,2'-bithien-5-yl group, a 2-(2-thiazolyl)thien-5-yl group, a 5-(2-thienyl)thiazol-2-yl group, and a 2,2',5',2''-terthien-5-yl group]

or a derivative thereof into DNA or RNA by chemical synthesis, wherein said method comprises:

synthesizing the DNA or RNA by using a phosphoramidite derivative of a nucleoside having an unnatural base represented by Formula I or a derivative thereof.

Advantageous Effects of Invention

The unnatural fluorescent base of the present invention emits strong fluorescence. Furthermore, it can form a base pair with a Pa derivative, an unnatural complementary base; hence, it can be introduced at a specific position of DNA or RNA by replication or transcription. Thus, the unnatural fluorescent base of the present invention establishes a novel method of fluorescent labeling of a nucleic acid.

In addition, the unnatural fluorescent base of the present invention shows excellent properties as a universal base. Since the universal base can form a base pair with any natural base in a double-stranded DNA or RNA, a functional nucleic acid can be labeled by substituting a natural base of a double-strand region in a nucleic acid structure with the unnatural base of the present invention.

BRIEF DESCRIPTION OF DRAWINGS

FIG. 2 illustrates differences in fluorescence intensity of nucleotides having unnatural bases, i.e., sTP, DssTP, and ssTP, A: a schematic diagram illustrating structures of the nucleotides, B: a photograph illustrating fluorescence emission in cuvettes when the nucleotides are excited at 365 nm, and C: fluorescent spectra.

FIG. 5 illustrates thermal stability of double-stranded DNA of a DNA fragment containing an unnatural base Dss and comparison with a known pyrrole-3-carboxamide (NP) base.

DESCRIPTION OF EMBODIMENTS

Figure 1:
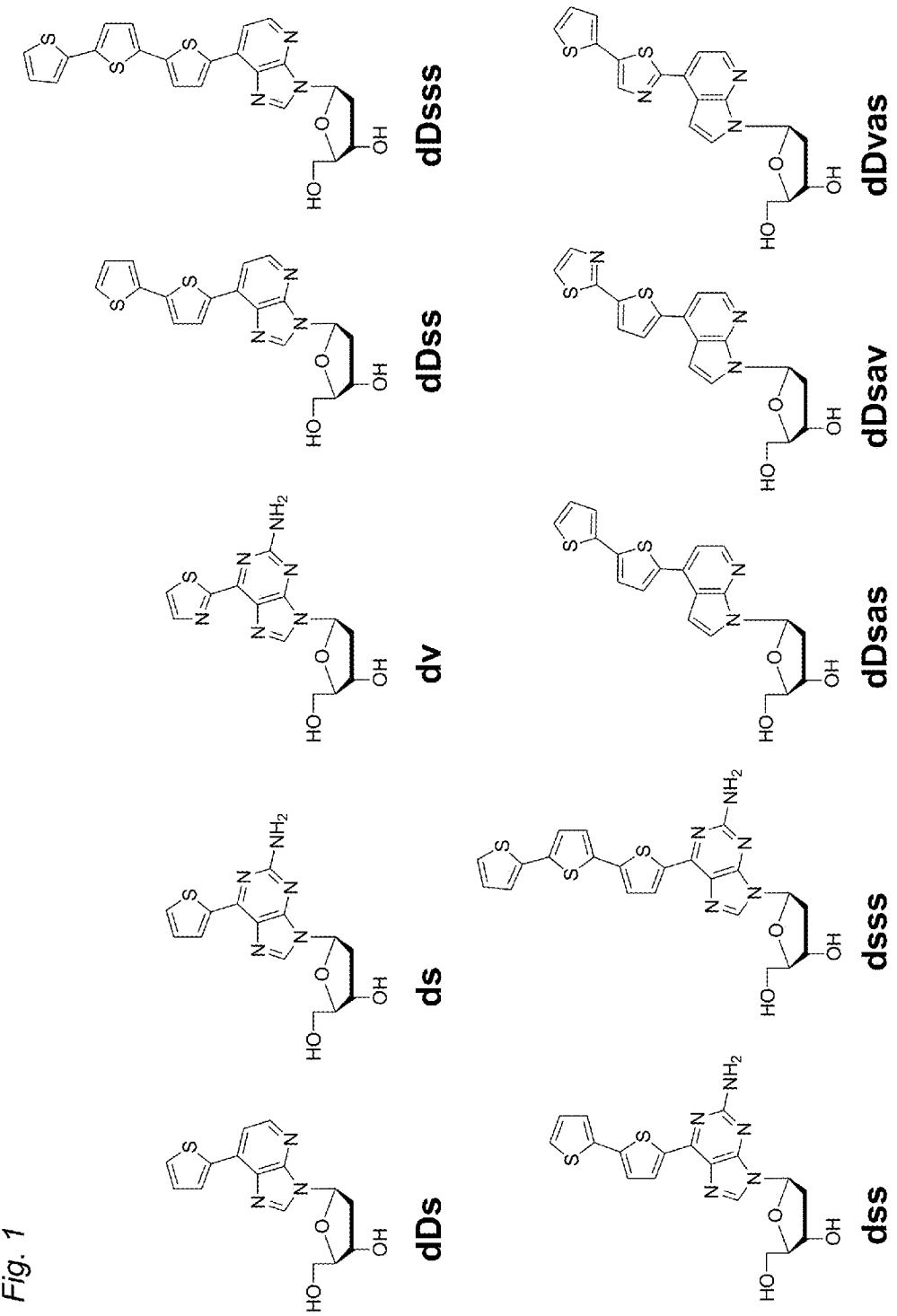
FIG. 1 illustrates structures of nucleosides having unnatural fluorescent bases.

The present invention will now be described in more detail.

DEFINITION

Unless otherwise specifically defined throughout the specification, the scientific terms and technical terms used in relation to the present invention are intended to have the same meanings as those generally used by those skilled in the art.

Throughout the specification, the term "nucleoside" refers to a glycosyl compound where a nucleic acid base and a reducing group of a carbohydrate are linked to each other by a glycoside bond. Here, the nucleic acid base is a concept including natural bases, i.e., adenine, guanine, cytosine, thymine, and uracil; modifications and analogs of the natural bases; and unnatural bases. The unnatural base refers to a functional group that is not a natural base, which can form a base pair with a natural base or another unnatural base in a nucleic acid in which the base is incorporated. Examples of the type of the unnatural base include, but not limited to, substituted or unsubstituted 2-aminopurine, substituted or unsubstituted imidazo[4,5-b]pyridine, substituted or unsubstituted pyrrolo[2,3-b]pyridine, substituted or unsubstituted pyridin-2-one, substituted or unsubstituted pyrrolo-2-carbaldehyde, and substituted or unsubstituted 2-nitropyrrole, isoguanine, isocytosine, xanthosine, 2,4-diaminopyrimidine, 4-methylbenzimidazole, difluorotoluene, propynyl isocarbostyril, and 7-azaindole. The unnatural base may be a derivative of a natural base.

Throughout the specification, the term "nucleotide" refers to an ester compound formed of the carbohydrate moiety of the nucleoside and phosphoric acid. The nucleotide is more preferably a mono-, di-, or tri-phosphate ester.

The carbohydrate moiety of a nucleoside or a nucleotide may be ribofuranosyl, 2'-deoxyribofuranosyl, or 2'-substituted ribofuranosyl having a substituent such as a halogen on the 2'-position. In the phosphate moiety, the hydroxyl group at the γ-position of the phosphate is preferably, but not limited, substituted with a group selected from the group consisting of amino groups, methylamino groups, dimethylamino groups, mercapto groups, and fluoro groups. The carbohydrate moiety of a nucleoside or a nucleotide and the phosphate moiety of a nucleotide are only required to have structures recognized in known nucleoside, nucleotide, and derivatives thereof. The ribonucleotide having a carbohydrate moiety of ribofuranosyl is a constituent of ribonucleic acid (RNA), and the deoxyribonucleotide having a carbohydrate moiety of 2'-deoxyribofuranosyl is a constituent of deoxyribonucleic acid (DNA).

Throughout the specification, examples of the derivative of the nucleoside or the nucleotide include phosphoramidite derivatives and H-phosphonate derivatives.

The phosphoramidite derivative is a nucleoside in which one or more substituents are modified with protecting groups and is used in chemical synthesis of a nucleic acid (for example, Sambrook et al., Molecular Cloning: A Laboratory Manual, 3rd Edition, Cold Spring Harbor Laboratory, NY: Cold Spring Harbor (2001), 10.42-10.46). Specifically, the 5'-hydroxyl group of (deoxy)ribose can be protected by a 5'-position protecting group that is used in nucleic acid synthesis, such as a dimethoxytrityl group (DMT), a monomethoxytrityl group, or a levulinyl group. This is because the 5'-hydroxyl group is prevented from reacting with phosphoramidite nucleoside that is fed for chemical synthesis of a nucleic acid. The tri-valent phosphate group linked to the (deoxy)ribose residue of the phosphoramidite nucleoside to be fed can be protected by, for example, a diisopropylamino group for activation by, for example, tetrazole during bond formation. The tri-valent phosphate group can be also linked to, for example, a cyanoethyl or methoxy for suppressing the reaction of a side chain. Furthermore, the amino group of a purine ring of a base can be protected by, for example, a phenoxyacetyl group or an isobutyryl group for protecting the nucleophilic function of an exocyclic amino group. The phosphoramidite derivative of the present invention has these protecting groups introduced at one or more positions. Preferably, protecting groups are introduced to all the positions described above.

Throughout the specification, the term "nucleic acid" refers to a molecule of a nucleic acid strand where one or more nucleotides are linked to each other in the 5'→3' direction. The nucleic acids of the present invention include single-stranded and double-stranded RNAs and DNAs. The double strand may be DNA/DNA, RNA/RNA, or DNA/RNA. The DNAs include cDNA formed by reverse transcription using RNA as a template. Furthermore, nucleic acid can form a triple strand and a quadruple strand, for example.

Throughout the specification, the term "universal base" refers to a base analog that forms a base pair with any natural base with substantially the same stability.

Compound Containing Unnatural Base or Derivative of the Unnatural Base

In an embodiment, the present invention provides a compound containing an unnatural base represented by the following Formula I:

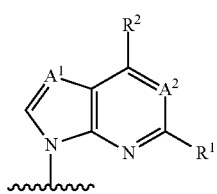

[wherein,
$A^1$ and $A^2$ each independently represent N or CH;
$R^1$ represents hydrogen or an amino group; and
$R^2$ represents a substituent selected from the group consisting of a 2,2'-bithien-5-yl group, a 2-(2-thiazolyl)thien-5-yl group, a 5-(2-thienyl)thiazol-2-yl group, and a 2,2',5',2"-terthien-5-yl group]
or a derivative thereof.

Throughout the specification, the derivatives of the unnatural base include derivatives of the unnatural bases of which functional groups are modified with protecting groups. Examples of the appropriate protecting group for protecting the amino group of an unnatural base include a phenoxyacetyl group, an isobutyryl group, and a dimethyl formamidyl group. The derivatives of the unnatural base may also include derivatives of the unnatural base represented by Formula I in which the thienyl group or the thiazolyl group contained in $R^2$ is further substituted with, for example, a methyl group, an amino group, a hydroxyl group, or a thiol group.

In another embodiment, the compound containing an unnatural base or a derivative thereof of the present invention may be represented by Formula II:

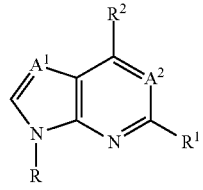

[wherein,
$A^1$ and $A^2$ each independently represent N or CH;
R is selected from the group consisting of hydrogen, a methyl group, carbohydrates, ribose, and deoxyribose;
$R^1$ represents hydrogen or an amino group; and
$R^2$ represents a substituent selected from the group consisting of a 2,2'-bithien-5-yl group, a 2-(2-thiazolyl)thien-5-yl group, a 5-(2-thienyl)thiazol-2-yl group, and a 2,2',5',2"-terthien-5-yl group].

Examples of the carbohydrate of substituent R include trioses such as dihydroxyacetone and glyceraldehyde; tetroses such as erythrulose, erythrose, and threose; pentoses such as ribulose, xylulose, ribose, arabinose, xylose, lixose, and deoxyribose; hexoses such as psicose, fructose, sorbose, tagatose, allose, altrose, glucose, mannose, gulose, idose, galactose, talose, fucose, fuculose, and rhamnose; and heptoses such as sedoheptulose. The carbohydrate of the substituent R may be further modified with another substituent.

In a preferred embodiment, the compound containing an unnatural base or a derivative thereof of the present invention includes a group selected from the group consisting of:
(i) a 7-(2,2'-bithien-5-yl)imidazo[4,5-b]pyridin-3-yl group (Dss);
(ii) a 7-(2,2',5',2"-terthien-5-yl)imidazo[4,5-b]pyridin-3-yl group (Dsss);
(iii) a 2-amino-6-(2,2'-bithien-5-yl)purin-9-yl group (ss);
(iv) a 2-amino-6-(2,2',5',2"-terthien-5-yl)purin-9-yl group (sss);
(v) a 4-(2,2'-bithien-5-yl)-pyrrolo[2,3-b]pyridin-1-yl group (Dsas);
(vi) a 4-[2-(2-thiazolyl)thien-5-yl]pyrrolo[2,3-b]pyridin-1-yl group (Dsav); and
(vii) a 445-(2-thienyl)thiazol-2-yl]pyrrolo[2,3-b]pyridin-1-yl group (Dvas).

Nucleoside and Nucleotide Having Unnatural Base

In an embodiment, the present invention provides a nucleoside or nucleotide having an unnatural base represented by the following Formula I:

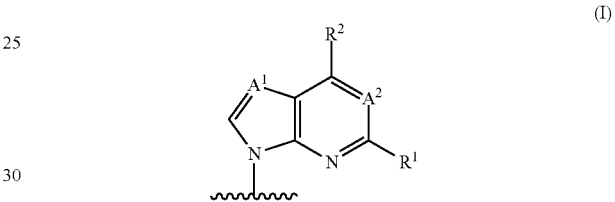

[wherein,
$A^1$ and $A^2$ each independently represent N or CH;
$R^1$ represents hydrogen or an amino group; and
$R^2$ represents a substituent selected from the group consisting of a 2,2'-bithien-5-yl group, a 2-(2-thiazolyl)thien-5-yl group, a 5-(2-thienyl)thiazol-2-yl group, and a 2,2',5',2"-terthien-5-yl group],
or a derivative thereof.

In a preferred embodiment, the present invention provides a nucleoside or nucleotide or a derivative thereof, wherein the unnatural base represented by the above-mentioned Formula I is selected from the group consisting of:
(i) a 7-(2,2'-bithien-5-yl)imidazo[4,5-b]pyridin-3-yl group (Dss);
(ii) a 7-(2,2',5',2"-terthien-5-yl)imidazo[4,5-b]pyridin-3-yl group (Dsss);
(iii) a 2-amino-6-(2,2'-bithien-5-yl)purin-9-yl group (ss);
(iv) a 2-amino-6-(2,2',5',2"-terthien-5-yl)purin-9-yl group (sss);
(v) a 4-(2,2'-bithien-5-yl)-pyrrolo[2,3-b]pyridin-1-yl group (Dsas);
(vi) a 4-[2-(2-thiazolyl)thien-5-yl]pyrrolo[2,3-b]pyridin-1-yl group (Dsav); and
(vii) a 445-(2-thienyl)thiazol-2-yl]pyrrolo[2,3-b]pyridin-1-yl group (Dvas).

The carbohydrate moiety of a nucleoside or nucleotide or a derivative thereof of the present invention may be ribofuranosyl, 2'-deoxyribofuranosyl, or 2'-substituted ribofuranosyl having a substituent such as a halogen on the 2'-position. In a preferred embodiment, the carbohydrate moiety is β-D-ribofuranosyl or 2-deoxy-β-D-ribofuranosyl.

The phosphate moiety of a nucleotide of the present invention is not particularly limited, and is preferably a tri-phosphate ester, i.e., deoxyribonucleoside 5'-triphosphate or ribonucleoside 5'-triphosphate.

Examples of the derivative of the nucleoside or nucleotide having an unnatural base of the present invention include not only phosphoramidite derivatives and H-phosphonate derivatives of the nucleoside or nucleotide having an unnatural base of the present invention but also derivatives where functional groups of the nucleoside or nucleotide are modified with protecting groups. Examples of the appropriate protecting group for protecting the amino group of the nucleoside or nucleotide having an unnatural base of the present invention include a phenoxyacetyl group, an isobutyryl group, and a dimethyl formamidyl group; and examples of the appropriate protecting group for protecting the hydroxyl group include an acetyl group, a tert-butyldimethylsilyl group, a tosyl group, a p-toluoyl group, a 4,4'-dimethoxytrityl group, a triisopropyl-silyloxymethyl group, a tetrahydropyranyl group, a tetrahydrofuranyl group, and a 2-(trimethylsilyl)ethoxymethyl group.

The nucleoside or nucleotide having an unnatural base or a derivative thereof of the present invention emits fluorescence by excitation at a wavelength of 200 nm or more, preferably 250 nm or more, 300 nm or more, 325 nm or more, 350 nm or more, 365 nm or more, or 370 nm or more. The unnatural base of the present invention has a functional group which consists of two or more heterocyclic moieties linked together, at the 6-position (the 6-position of purine ring) of a purine base, a 1-deazapurine base, or a 1,7-deazapurine base and, thereby, particularly shows strong fluorescence by excitation at a wavelength of 350 nm or more. Such fluorescence characteristics enable an operation to detect a pmol level with the naked eye.

The unnatural base of the present invention can be used as a universal base.

Method of Introducing Unnatural Base: Method Involving Replication, Transcription, or Reverse Transcription The present invention also provides a method of introducing an unnatural base or a derivative thereof of the present invention into DNA or RNA by replication of a nucleic acid, wherein said method comprises using a template strand which is a nucleic acid containing a nucleotide having a base represented by Formula III (hereinafter referred to as Pa derivative):

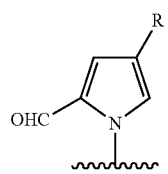

(III)

[wherein,

R is selected from the group consisting of hydrogen and substituted or unsubstituted alkyl, alkenyl, and alkynyl groups, wherein the substituent of the substituted alkyl, alkenyl, or alkynyl group is a functional group or a fluorescent functional group];
conducting replication, transcription, or reverse transcription of a nucleic acid by using deoxyribonucleoside 5'-triphosphate or ribonucleoside 5'-triphosphate including an unnatural base represented by Formula I as a replication substrate; and thereby a nucleic acid containing a base pair of the base Pa derivative and the unnatural base represented by Formula I is generated and a nucleotide having the unnatural base represented by Formula I is introduced into DNA or RNA.

Figure 3:
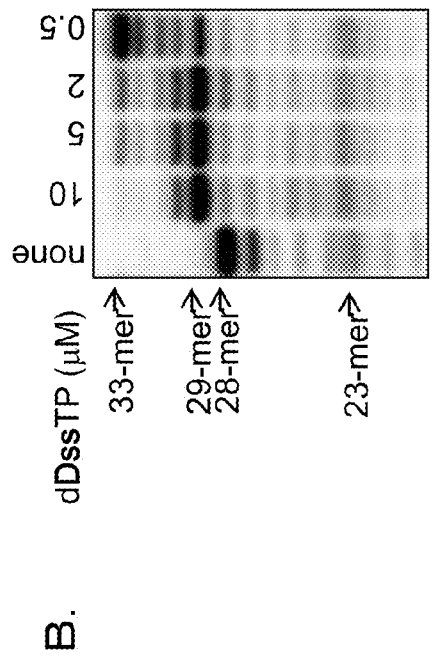
FIG. 3 illustrates incorporation of an unnatural base Dss into DNA by replication using a Klenow fragment (exo+), A: a schematic diagram illustrating replication, and B: a gel electrophoresis photograph illustrating analytical results.
Figure 4:
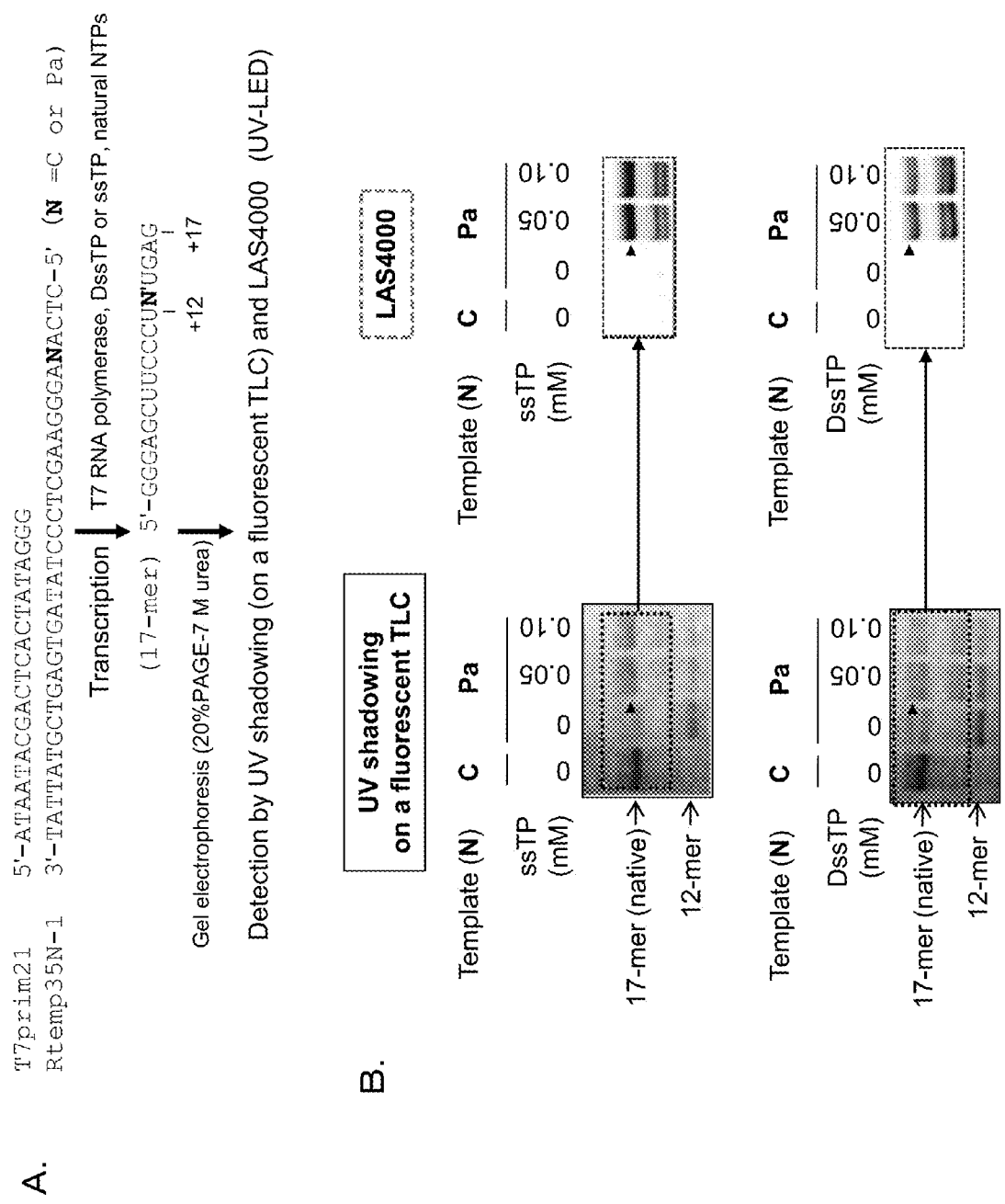
FIG. 4 illustrates incorporation of unnatural bases ss and Dss into RNA by transcription using T7 RNA polymerase, A: a schematic diagram illustrating transcription and an analysis procedure, and B: gel electrophoresis photographs illustrating analytical results (left: detection by UV shadowing, right: detection by epi-UV LED).

The unnatural base of the present invention can form a base pair with another unnatural base, i.e., a Pa derivative. The unnatural base of the present invention is incorporated into DNA or RNA by incorporating a Pa derivative, which is a complementary base of the unnatural base of the present invention, into a template strand DNA, and performing complementation of the unnatural base of the present invention to the Pa derivative in the template DNA by nucleic acid replication using a DNA polymerase, an RNA polymerase, or a reverse transcriptase (FIGS. 3 and 4). That is, the unnatural base of the present invention can be selectively introduced into a specific position of DNA or RNA by complementing to Pa in the template DNA.

The replication, transcription, and reverse transcription of nucleic acid in the method of the present invention can be performed by a known method. Those skilled in the art can appropriately determine reaction conditions, such as selection of enzyme, selection of substrate concentration, and selection of annealing conditions, and such determination is within a range of matters that are routinely performed by those skilled in the art. However, the concentration ratio of an unnatural base to a nucleotide substrate during replication, transcription, or reverse transcription of nucleic acid is preferably lower than that of each natural base to a nucleotide substrate for performing efficient replication, transcription, and reverse transcription of nucleic acid. For example, the concentration ratio of an unnatural base to the nucleotide substrate is ½ or less, ⅕ or less, 1/10 or less, 1/20 or less, or 1/100 or less of that of each natural base to the nucleotide substrate.

Examples of the DNA polymerase that can be used for introduction of an unnatural base of the present invention into DNA by replication include the Klenow fragment of *Escherichia coli*, T4 DNA polymerase, Phi29 DNA polymerase, Bst DNA polymerase, and heat-resistant polymerases such as Pfu, DeepVent, Vent, Titanium Taq, and KlenTaq. In the replication, the nucleotide having the unnatural base of the present invention that can be used as a substrate is deoxyribonucleoside-5'-triphosphate.

Examples of the RNA polymerase that can be used for introduction of an unnatural base of the present invention into RNA by transcription include phage-derived RNA polymerases such as T7 RNA polymerase, T3 RNA polymerase, and SP6 RNA polymerase and RNA-dependent RNA polymerases such as Qβ replicase. In the transcription, the nucleotide having the unnatural base of the present invention that can be used as a substrate is ribonucleoside-5'-triphosphate.

Examples of the reverse transcriptase that can be used for introduction of an unnatural base of the present invention into DNA by reverse transcription include reverse transcriptases derived from HIV, AMV, or MMLV. In the reverse transcription, the nucleotide having the unnatural base of the present invention that can be used as a substrate is deoxyribonucleoside-5'-triphosphate.

Method of Introducing Unnatural Base: Method by Chemical Synthesis

The present invention also provides a method of introducing an unnatural base or a derivative thereof of the present invention into DNA or RNA by chemical synthesis. The method includes synthesis of DNA or RNA using a phosphoramidite, H-phosphonate, or triphosphate derivative of nucleoside having an unnatural base represented by Formula I or a derivative thereof.

The method of synthesizing DNA or RNA using a phosphoramidite, H-phosphonate, or triphosphate derivative of nucleoside is known to those skilled in the art. Those skilled in the art can determine reaction conditions suitable for an unnatural base or a derivative thereof of the present invention.

Nucleic Acid Containing Nucleotide of the Present Invention

The present invention also provides a nucleic acid into which a nucleotide having an unnatural base of the present invention is incorporated. The nucleic acid of the present invention can be prepared by a method of introducing a nucleotide into DNA or RNA by the above-described replication of nucleic acid. Alternatively, the nucleic acid of the present invention can be prepared by incorporating a nucleotide into DNA or RNA by chemical synthesis. Examples of the chemical synthesis include a phosphoramidite method, a phosphonate method, and a triphosphate method.

A nucleic acid containing a nucleotide having an unnatural base of the present invention emits fluorescence by excitation at a wavelength of 200 nm or more, preferably 250 nm or more, 300 nm or more, 325 nm or more, 350 nm or more, 365 nm or more, or 370 nm or more. The unnatural base of the present invention has a functional group which consists of two or more heterocyclic moieties linked together, at the 6-position (the 6-position of purine ring) of a purine base, a 1-deazapurine base, or a 1,7-deazapurine base and, thereby, shows strong fluorescence by excitation, in particular, even at a wavelength of 350 nm or more. Such fluorescence characteristics enable an observer to detect the pmol level with the naked eye. That is, the nucleic acid containing a nucleotide having an unnatural base of the present invention can be used as a fluorescent probe.

In a preferred embodiment, the nucleic acid containing a nucleotide having an unnatural base of the present invention is a functional nucleic acid selected from the group consisting of antisense DNAs, antisense RNAs, ribozymes, deoxyribozymes, RNA interference-inducing nucleic acids such as siRNAs and shRNAs, microRNAs, antimicroRNA nucleic acid molecules, decoy nucleic acids, DNA aptamers, and RNA aptamers.

The antisense DNA and RNA are nucleic acids complementary to a part of a mRNA. The antisense DNA and RNA can inhibit translation of an mRNA by binding to the mRNA.

The ribozyme is the generic name for RNAs having catalytic activities, and the deoxyribozyme is the generic name for DNAs having catalytic activities.

The RNA interference (RNAi) is a phenomenon where a double-stranded RNA (dsRNA) inhibits the expression of a gene by sequence-specific degradation of a mRNA having a sequence corresponding to that of the dsRNA. For example, in typical RNA interference, a dsRNA is processed by Dicer, which belongs to an RNase III family, into short interfering RNAs (siRNAs) of about 21 to 23 bases having an overhang of about two bases at the 3'-end. The siRNA is incorporated into an siRNA-protein complex called RISC to sequence-specifically degrade a mRNA having a sequence corresponding to the sequence of the siRNA. It has been shown that the RNA interference is a phenomenon that is widely conserved in various species such as mammals (e.g., human and mouse), nemotodes, plants, *drosophila*, and fungi. The RNA interference-inducing nucleic acid containing a nucleotide having an unnatural base of the present invention can be used as an siRNA or short hairpin RNA (shRNA) in RNA interference.

The microRNA is an RNA composed of several tens of bases not encoding protein, but having a function of regulating gene expression. The anti-microRNA nucleic acid molecule acts on a microRNA to modulate the gene expression-regulating function of the microRNA.

The decoy nucleic acid is a double-stranded nucleic acid having the same sequence as that of the binding site on the DNA of a transcription factor. The decoy nucleic acid can capture a transcription factor protein and thereby inhibit the expression of a gene that is inherently regulated by the transcription factor.

The DNA aptamer and the RNA aptamer are single-stranded nucleic acids each selected so as to bind to a specific target substance by, for example, a SELEX method.

In another preferred embodiment, the nucleic acid containing a nucleotide having an unnatural base of the present invention may be an amplification primer used in nucleic acid amplification methods such as LAMP (loop-mediated isothermal amplification) method, SDA (standard displacement amplification) method, SMAP (smart amplification process), NASBA (nucleic acid sequence-based amplification) method, ICAN (isothermal and chimeric primer-initiated amplification of nucleic acids), UCAN method, TMA method, Padlock Probe method, RCA (rolling circle) method, bDNA (a branched DNA) method, PALSAR (probe alternation link self-assembly reaction) method, Invader method, TRC (transcription reverse transcription concerted reaction) method, CPT (cycling probe technology) method, and Plexor method.

In another preferred embodiment, the nucleic acid containing a nucleotide having an unnatural base of the present invention may be a probe for detecting a target nucleic acid, such as a molecular beacon, Taqman probe, Scorpion-based probe, or Riboswitch.

Nucleic Acid Mimic Containing Nucleotide of the Present Invention

The present invention also provides a nucleic acid mimic including an unnatural base or a derivative thereof of the present invention. Examples of the nucleic acid mimic include morpholino-nucleotides, locked nucleic acids (LNAs), and peptide nucleic acids (PNAs).

The nucleic acid mimic is a mimic where the backbone structure composed of riboses or deoxyriboses linked by phosphate ester bonds of a natural nucleic acid is replaced by another backbone structure.

The morpholino-nucleotide has a backbone of the following structure:

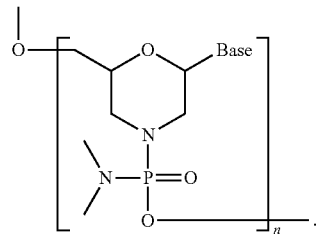

The locked nucleic acid (LNA) has a backbone of the following structure:

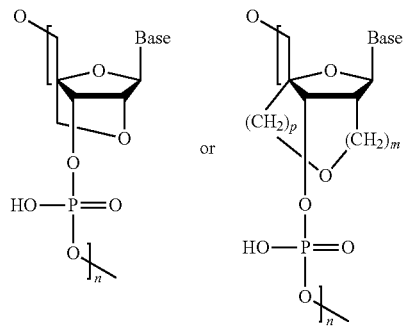

[wherein, m is an integer of 0 to 2; and p is an integer of 1 to 3], or

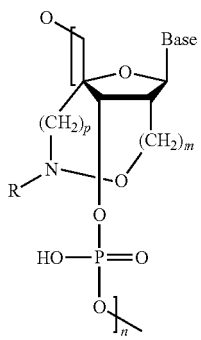

[wherein, m is an integer of 0 to 2; p is an integer of 1 to 3; and R represents a hydrogen atom, an alkyl group, an alkenyl group, a cycloalkyl group, an aryl group, an aralkyl group, an acyl group, or a sulfonyl group].

The peptide nucleic acid (PNA) has a backbone of the following structure:

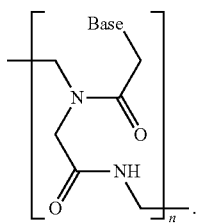

The method of synthesizing the backbone structure of each nucleic acid mimic is known to those skilled in the art, and the unnatural base of the present invention can be applied to the backbone structures of these nucleic acid mimics.

Unnatural Base as Universal Base

The present inventors have found that the unnatural base of the present invention shows a property as a universal base, that is, the unnatural base can form a stable base pair with any natural base in a double-stranded DNA.

The stability of the base pairing between an unnatural base of the present invention and a natural base can be evaluated through thermal stability by introducing the unnatural base of the present invention into the center of a DNA fragment having a certain length, incorporating the natural base at the corresponding position of a complementary strand, and measuring the Tm values of the respective double-stranded DNAs.

The DNA fragment containing a nucleotide having the unnatural base of the present invention forms a double strand with a complementary DNA thereof. The thermal stability of the double-stranded DNA is substantially the same in any base pair of the unnatural base of the present invention and a natural base. In addition, the stability is higher than a T-G base pair, which is the most stable mismatched base pair between natural bases.

The particularly useful unnatural bases serving as universal bases are 7-(2,2'-bithien-5-yl)imidazo[4,5-b]pyridin-3-yl group (Dss) and 2-amino-6-(2,2'-bithien-5-yl)purin-9-yl group (ss).

The unnatural base of the present invention can form a base pair with any natural base in a double-stranded DNA or RNA.

Accordingly, a natural base of a double-strand region in a nucleic acid structure can be substituted with the unnatural base. Thus, even in a functional nucleic acid including a region for forming a double strand, a natural base can be substituted with the unnatural base of the present invention.

By combining the other characteristics of the unnatural base of the present invention, that is, emission of strong fluorescence and the ability of being introduced into a specific position in DNA or RNA by replication or transcription through formation of a base pair with a Pa derivative as an unnatural complementary base, the unnatural base of the present invention can be used in various basic and applied researches such as site-specific labeling of DNA or RNA with fluorescence, analysis of local structure of nucleic acid conformation, fluorescence labeling and dynamic analysis (imaging) of nucleic acid drugs, real time PCR, and SNP analysis. No fluorescent base analog having these properties has been reported yet.

EXAMPLES

The present invention will be more specifically described by the following examples, which are not intended to limit the technical scope of the present invention. Those skilled in the art can easily add modifications or changes to the present invention on the basis of the description of this specification, and such modifications and changes are included in the technical scope of the present invention.

Reagent, Solvent, and Other Components

Reagents and solvents were purchased from typical suppliers and were used without further purification. $^1$H-NMR (300 MHz, 270 MHz) and $^{31}$P-NMR (121 MHz) spectra were recorded on a BRUKER AV300 or JEOL nuclear magnetic resonance spectrometer. Synthesized nucleoside derivatives and nucleoside 5'-triphosphate were purified with a Gilson HPLC system using a fractionation column (Waters Microbond Sphere, C18, 19 mm×150 mm, flow rate: 10 mL/min) and a fractionation column (PEGASIL C8, Senshu Scientific Co., Ltd., 10 mm×150 mm, flow rate: 6 mL/min), respectively. Electrospray-ionization mass spectra (ESI-MS) were recorded on a Waters ZMD 4000 mass system equipped with a Waters 2690 LC system. Fluorescence spectra were measured with a JASCO FP6500 fluorescence spectrometer, and fluorescence quantum yields were determined using quinine sulfate as a standard.

Example 1

Synthesis of nucleoside; synthesis of 7-(2,2'-bithien-5-yl)-3-(2-deoxy-β-D-ribofuranosyl)imidazo[4,5-b]pyridine (dDss) and 7-(2,2',5',2''-terthien-5-yl)-3-(2-deoxy-β-D-ribofuranosyl)imidazo[4,5-b]pyridine (dDsss)

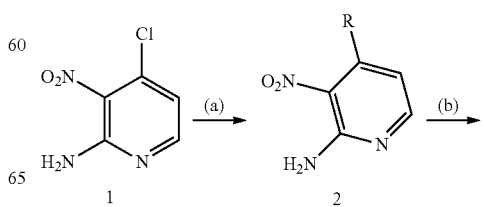

-continued

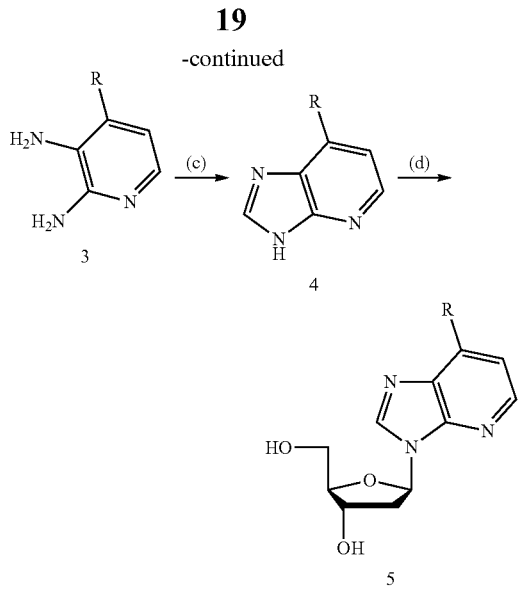

Conditions:
(a) 5-tributylstannyl-2,2'-bithiophene or 5-tributylstannyl-2,2',5',2''-terthiophene, Pd(PPh₃)₂Cl₂, and DMF;
(b) Pd/C, NaBH₄, pyridine, and H₂O;
(c) HCOOH; and
(d) NaH, 2-deoxy-3,5-di-O-p-toluoyl-α-D-erythro-pentofuranosyl chloride, and CH₃CN, and then NaOMe, MeOH, and CH₂Cl₂.
R represents a 2,2'-bithien-5-yl group or a 2,2',5',2''-terthien-5-yl group.

(1-1) Synthesis of 4-(2,2'-bithien-5-yl)-3-nitropyridine-2-amine and 4-(2,2',5',2''-terthien-5-yl)-3-nitropyridine-2-amine Normal-butyllithium (1.57 M solution in hexane: 3.2 mL, 5.0 mmol) was added to a solution of 2,2'-bithiophene (830 mg, 5.0 mmol) in THF (50 mL) at −78° C. This solution was stirred at −78° C. for 30 min, and then tributylstannyl chloride (1.5 mL) was added thereto. The reaction solution was stirred at room temperature for 30 min and was then separated between water and ethyl acetate. The organic layer was washed with saturated brine and dried over anhydrous sodium sulfate. The organic layer was concentrated and was then added to a solution of 2-amino-3-nitro-4-chloropyridine (519 mg, 3.0 mmol) and dichlorobis(triphenylphosphine)palladium (105 mg, 0.15 mmol) in DMF (18 mL). This solution was stirred at 100° C. for 5 hr and was then separated between ethyl acetate and water. The organic layer was washed with water, dried over anhydrous sodium sulfate, and concentrated under reduced pressure. 4-(2,2'-Bithien-5-yl)-3-nitropyridine-2-amine (809 mg, 89%) was obtained through purification by silica gel column chromatography (elution with a solution of 2% ethyl acetate in methylene chloride).

4-(2,2',5',2''-Terthiophen-5-yl)-3-nitropyridine-2-amine (250 mg, yield: 22%) was synthesized using 2,2',5',2''-terthiophene (1.24 g, 5.0 mmol) by the same reaction.

4-(2,2'-Bithien-5-yl)-3-nitropyridine-2-amine: ¹H NMR (300 MHz, DMSO-d₆) δ 8.19 (d, 1H, J=5.1 Hz), 7.60 (dd, 1H, J=1.1, 5.1 Hz), 7.41 (dd, 1H, J=1.2, 3.6 Hz), 7.35 (d, 1H, J=3.8 Hz), 7.20 (d, 1H, J=3.9 Hz), 7.14 (dd, 1H, J=3.6, 5.1 Hz), 6.97 (bs, 1H), 6.80 (d, 1H, J=5.1 Hz). HRMS (FAB, 3-NBA matrix) for C₁₃H₁₀N₃O₂S₂, (M+H)⁺ calculated value: 304.0214, observed value: 304.0172.

4-(2,2',5',2''-Terthien-5-yl)-3-nitropyridine-2-amine: ¹H NMR (300 MHz, DMSO-d₆) δ 8.19 (d, 1H, J=5.0 Hz), 7.57 (dd, 1H, J=1.1, 5.1 Hz), 7.40 (m, 3H), 7.32 (d, 1H, J=3.8 Hz), 7.22 (d, 1H, J=3.9 Hz), 7.13 (dd, 1H, J=3.7, 5.1 Hz), 6.99 (bs, 2H), 6.80 (d, 1H, J=5.0 Hz).

(1-2) Synthesis of 4-(2,2'-bithien-5-yl)pyridine-2,3-diamine and 4-(2,2',5',2''-terthien-5-yl)pyridine-2,3-diamine One mole of NaBH₄ (7.5 mL) was added to a solution of 4-(2,2'-bithien-5-yl)-3-nitropyridine-2-amine (760 mg, 2.5 mmol) and palladium (10% carbon) in pyridine (25 mL) at 0° C. The solution was stirred at 0° C. for 30 min, and an aqueous of 5% ammonium chloride solution was added thereto. The solution was stirred for 5 min and was then filtered. The filtrate was separated between methylene chloride and water, and the organic layer was dried over anhydrous sodium sulfate and concentrated. 4-(2,2'-Bithien-5-yl)pyridine-2,3-diamine (448 mg, 65%) was obtained through purification by silica gel column chromatography (elution with a solution of 5% methanol in methylene chloride).

4-(2,2',5',2''-Terthien-5-yl)pyridine-2,3-diamine (103 mg, yield: 45%) was synthesized using 4-(2,2',5',2''-terthien-5-yl)-3-nitropyridine-2-amine (250 mg, 0.65 mmol) by the same reaction.

4-(2,2'-Bithien-5-yl)pyridine-2,3-diamine: ¹H NMR (300 MHz, DMSO-d₆) δ 7.54 (dd, 1H, J=7.54 Hz), 7.36-7.32 (m, 4H), 7.12 (dd, 1H, J=3.6, 5.1 Hz), 6.51 (d, 1H, J=5.3 Hz), 5.70 (bs, 2H), 4.77 (bs, 2H). HRMS (FAB, 3-NBA matrix) for C₁₃H₁₂N₃S₂, (M+H)⁺ calculated value: 274.0473, observed value: 274.0470.

4-(2,2',5',2''-Terthien-5-yl)pyridine-2,3-diamine: ¹H NMR (300 MHz, DMSO-d₆) δ 7.55 (dd, 1H, J=1.1, 5.1 Hz), 7.39-7.29 (m, 6H), 7.12 (dd, 1H, J=3.6, 5.1 Hz), 6.52 (d, 1H, J=5.3 Hz), 5.71 (bs, 2H), 4.79 (bs, 2H).

(1-3) Synthesis of 7-(2,2'-bithien-5-yl)-3H-imidazo[4,5-b]pyridine and 7-(2,2',5',2''-terthien-5-yl)-3H-imidazo[4,5-b]pyridine A solution of 4-(2,2'-bithien-5-yl)pyridine-2,3-diamine (273 mg, 1.0 mmol) in formic acid (3.0 mL) was refluxed at 140° C. for 12 hr. The reaction solution was cooled to 0° C. and was then added to a 28% aqueous ammonia (5.0 mL). This solution was separated between ethyl acetate and water, and the organic layer was washed with water, dried over anhydrous sodium sulfate, and dried under reduced pressure to yield 7-(2,2'-bithien-5-yl)-3H-imidazo[4,5-b]pyridine (272 mg, 96%).

7-(2,2',5',2''-Terthien-5-yl)-3H-imidazo[4,5-b]pyridine (106 mg, yield: 99%) was synthesized using 4-(2,2',5',2''-terthien-5-yl)pyridine-2,3-diamine (100 mg, 0.29 mmol) by the same reaction.

7-(2,2'-Bithien-5-yl)-3H-imidazo[4,5-b]pyridine: ¹H NMR (300 MHz, DMSO-d₆) δ 13.25 (bs, 1H), 8.50 (s, 1H), 8.32 (s, 1H, J=5.2 Hz), 8.22 (d, 1H, J=3.9 Hz), 7.61 (d, 1H, J=5.0H), 7.59 (dd, 1H, J=5.0, 6.2 Hz), 7.47 (dd, 1H, J=1.1, 3.6 Hz), 7.45 (d, 1H, J=4.1 Hz), 7.15 (dd, 1H, J=3.6, 5.1 Hz). HRMS (FAB, 3-NBA matrix) for C₁₄H₁₀N₃S₂, (M+H)⁺ calculated value: 284.0316, observed value: 284.0365.

7-(2,2',5',2''-Terthien-5-yl)-3H-imidazo[4,5-b]pyridine: ¹H NMR (300 MHz, DMSO-d₆) δ 13.25 (bs, 1H), 8.51 (s, 1H), 8.33 (d, 1H, J=5.2 Hz), 8.23 (d, 1H, J=4.0 Hz), 7.62 (d, 1H, J=5.3H), 7.57 (dd, 1H, J=1.2, 5.1 Hz), 7.50 (d, 1H, J=3.9 Hz), 7.44 (d, 1H, J=3.8 Hz), 7.40 (dd, 1H, J=1.2, 3.6 Hz), 7.34 (d, 1H, J=3.8 Hz), 7.13 (dd, 1H, J=3.6, 5.1).

(1-4) Synthesis of 7-(2,2'-bithien-5-yl)-3-(2-deoxy-β-D-ribofuranosyl)imidazo[4,5-b]pyridine (dDss) and 7-(2,2',5',2''-terthien-5-yl)-3-(2-deoxy-β-D-ribofuranosyl)imidazo[4,5-b]pyridine (dDsss)

NaH (24 mg, 0.6 mmol, 60% dispersion in mineral oil) was added to a solution of 7-(2,2'-bithien-5-yl)-3H-imidazo[4,5-b]pyridine (142 mg, 0.5 mmol) in CH$_3$CN (10 mL). The reaction solution was stirred at room temperature for 30 min and then at 40° C. for 30 min, and 2-deoxy-3,5-di-O-p-toluoyl-α-D-erythro-pentofuranosyl chloride (233 mg, 0.6 mmol) was added thereto at room temperature. This reaction solution was stirred at room temperature for 12 hr and was separated between ethyl acetate and water. The organic layer was washed with saturated brine, dried over anhydrous sodium sulfate, and concentrated under reduced pressure. 7-(2,2'-Bithien-5-yl)-3-(2-deoxy-3,5-di-O-toluoyl-β-D-ribofuranosyl)imidazo[4,5-b]pyridine (227 mg, 0.36 mmol) was obtained through purification by silica gel column chromatography (elution with a solution of 2% methanol in methylene chloride). A solution of 28% NaOCH$_3$ in methanol (208 mg) was added to a solution of 7-(2,2'-bithien-5-yl)-3-(2-deoxy-3,5-di-O-toluoyl-β-D-ribofuranosyl)imidazo[4,5-b]pyridine (227 mg, 0.36 mmol) in methylene chloride (3.5 mL) and methanol (3.5 mL), followed by stirring at room temperature for 30 min. The reaction solution was separated between ethyl acetate and an aqueous saturated ammonium chloride solution, and the organic layer was washed with water, dried over anhydrous sodium sulfate, and concentrated under reduced pressure. 7-(2,2'-Bithien-5-yl)-3-(2-deoxy-β-D-ribofuranosyl)imidazo[4,5-b]pyridine (90 mg, 45%, second-stage yield) was obtained through purification by silica gel column chromatography (elution with a solution of 2% methanol in methylene chloride) and then by RP-HPLC.

7-(2,2',5',2''-Terthien-5-yl)-3-(2-deoxy-β-D-ribofuranosyl)imidazo[4,5-b]pyridine (22 mg, 17%, second-stage yield) was synthesized using 7-(2,2',5',2''-terthien-5-yl)-3H-imidazo[4,5-b]pyridine (100 mg, 0.27 mmol) by the same reaction (excepting that NaH was added and reflux was performed for 12 hr).

7-(2,2'-Bithien-5-yl)-3-(2-deoxy-β-D-ribofuranosyl)imidazo[4,5-b]pyridine: $^1$H NMR (300 MHz, DMSO-d$_6$) δ 8.77 (s, 1H), 8.35 (d, 1H, J=5.2 Hz), 8.23 (d, 1H, J=3.9 Hz), 7.68 (d, 1H, J=5.2 Hz), 7.60 (dd, 1H, J=1.0, 5.1 Hz), 7.48-7.45 (m, 2H), 7.15 (dd, 1H, J=3.7, 5.1 Hz), 6.54 (t, 1H, J=6.8 Hz), 5.34 (d, 1H, J=4.1 Hz), 5.11 (t, 1H, J=5.8 Hz), 4.47 (m, 1H), 3.92 (m, 1H), 3.69-3.52 (m, 2H), 2.81 (m, 1H), 2.36 (ddd, 1H, J=3.3, 6.2, 13.2 Hz). $^{13}$C NMR (75 MHz, DMSO-d$_6$) δ 147.06, 144.01, 143.65, 140.02, 136.11, 135.50, 131.45, 130.82, 129.95, 128.56, 126.24, 124.74, 124.55, 113.51, 87.89, 83.77, 70.78, 61.71, 39.39. HRMS (FAB, 3-NBA matrix) for C$_{19}$H$_{18}$N$_3$O$_3$S$_2$, (M+H)$^+$ calculated value: 400.0790, observed value: 400.0815.

7-(2,2',5',2''-Terthien-5-yl)-3-(2-deoxy-β-D-ribofuranosyl)imidazo[4,5-b]pyridine: $^1$H NMR (300 MHz, DMSO-d$_6$) δ 8.77 (s, 1H), 8.36 (d, 1H, J=5.2 Hz), 8.24 (d, 1H, J=4.0 Hz), 7.70 (d, 1H, J=5.2 Hz), 7.57 (dd, 1H, J=1.1, 5.1 Hz), 7.51 (d, 1H, J=3.9 Hz), 7.45 (d, 1H, J=3.8 Hz), 7.40 (dd, 1H, J=1.1, 3.6 Hz), 7.34 (d, 1H, J=3.8 Hz), 7.13 (dd, 1H, J=3.6, 5.1 Hz), 6.54 (t, 1H, J=6.8 Hz), 5.34 (d, 1H, J=2.4 Hz), 5.11 (t, 1H, J=5.3 Hz), 4.46 (m, 1H), 3.92 (m, 1H), 3.60 (m, 2H), 2.81 (m, 1H), 2.36 (ddd, 1H, J=3.3, 6.2, 13.2 Hz).

Example 2

Synthesis of nucleoside; synthesis of 2-amino-6-(2,2'-bithien-5-yl)-9-(2-deoxy-β-D-ribofuranosyl)purine (dss) and 2-amino-6-(2,2',5',2''-terthien-5-yl)-9-(2-deoxy-β-D-ribofuranosyl)purine (dsss)

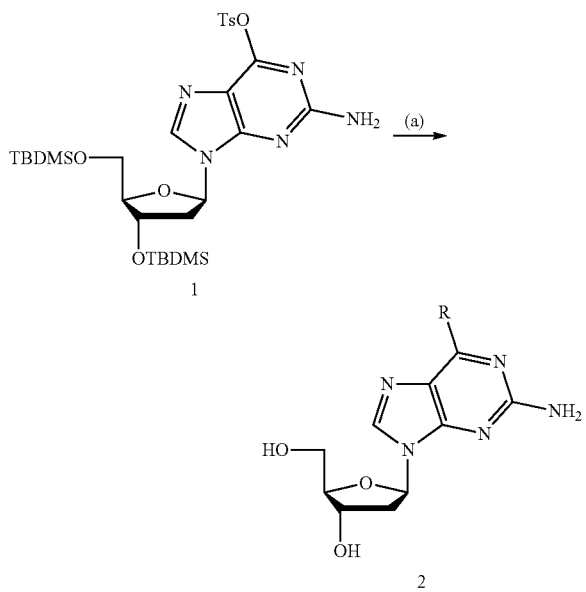

Conditions:
(a) 5-tributylstannyl-2,2'-bithiophene or 5-tributylstannyl-2,2',5',2''-terthiophene, Pd(PPh$_3$)$_4$, LiCl, and dioxane, and then TBAF and THF.
R represents a 2,2'-bithien-5-yl group or a 2,2',5',2''-terthien-5-yl group.

A solution of 6-O-tosyl-3',5'-di-O-tert-butyldimethylsilyl-deoxyguanosine (650 mg, 1.0 mmol), tetrakis(triphenylphosphine)palladium (58 mg, 0.05 mmol), lithium chloride (84 mg, 2.0 mmol), and 5-tributylstannyl-2,2'-bithiophene (5.0 mmol) in dioxane was refluxed at 120° C. for 4.5 hr. The reaction solution was separated between ethyl acetate and water, and the organic layer was washed with water, dried over anhydrous sodium sulfate, and concentrated under reduced pressure. 2-Amino-6-(2,2'-bithien-5-yl)-9-(2-deoxy-3,5-di-O-tert-butyldimethylsilyl-β-D-ribofuranosyl)purine (550 mg, 86%) was purified by silica gel column chromatography (elution with a solution of 1% methanol in methylene chloride). A solution of 1 M of tetrabutylammonium fluoride in THF (2.6 mL) was added to a solution of 2-amino-6-(2,2'-bithien-5-yl)-9-(2-deoxy-3,5-di-O-tert-butyldimethylsilyl-β-D-ribofuranosyl)purine (550 mg) in THF (8.6 mL), followed by stirring at room temperature for 1 hr. The reaction solution was concentrated, and then 2-amino-6-(2,2'-bithien-5-yl)-9-(2-deoxy-β-D-ribofuranosyl)purine (264 mg, 64%, second stage yield) was obtained through purification by silica gel column chromatography and RP-HPLC.

2-Amino-6-(2,2',5',2''-terthien-5-yl)-9-(2-deoxy-β-D-ribofuranosyl)purine (dsss) (405 mg, 81%, second stage yield) was synthesized using 5-tributylstannyl-2,2',5',2''-terthiophene (5.0 mmol) by the same reaction.

2-Amino-6-(2,2'-bithien-5-yl)-9-(2-deoxy-β-D-ribofuranosyl)purine (dss): $^1$H NMR (300 MHz, DMSO-d$_6$) δ 8.45 (d, 1H, J=3.9 Hz), 8.38 (s, 1H), 7.61 (dd, 1H, J=1.1, 5.1 Hz), 7.48-7.46 (m, 2H), 7.16 (dd, 1H, J=3.7, 5.1 Hz), 6.57 (bs, 2H), 6.29 (t, 1H, J=7.4 Hz), 5.30 (d, 1H, J=4.1 Hz), 4.98 (t, 1H, J=5.5 Hz), 4.40 (m, 1H), 3.85 (m, 1H), 3.58 (m, 2H), 2.66 (m, 1H), 2.28 (m, 1H).

2-Amino-6-(2,2',5',2''-terthien-5-yl)-9-(2-deoxy-β-D-ribofuranosyl)purine (dsss): $^1$H NMR (270 MHz, DMSO-$d_6$) δ 8.44 (d, 1H, J=4 Hz), 8.37 (s, 1H), 7.56 (dd, 1H, J=1.1, 4.9 Hz), 7.49 (d, 1H, J=4.0 Hz), 7.43 (d, 1H, J=4.0 Hz), 7.39 (dd, 1H, J=1.0, 3.6 Hz), 7.32 (d, 1H, J=4.0 Hz), 7.12 (dd, 1H, J=3.6, 4.9 Hz), 6.56 (bs, 2H), 6.28 (t, 1H, J=6.9 Hz), 5.29 (d, 1H, J=4.0 Hz), 4.96 (t, 1H, J=5.6 Hz), 4.38 (m, 1H), 3.85 (m, 1H), 3.55 (m, 2H), 2.65 (m, 1H), 2.28 (m, 1H).

Example 3

Synthesis of nucleoside; synthesis of 1-[2-deoxy-β-D-ribofuranosyl]-4-(2,2'-bithien-5-yl)-pyrrolo[2,3-b]pyridine (dDsas), 1-[2-deoxy-β-D-ribofuranosyl]-4-[2-(2-thiazolyl)thien-5-yl]pyrrolo[2,3-b]pyridine (dDsav), and 1-[2-deoxy-β-D-ribofuranosyl]-4-[5-(2-thienyl)thiazol-2-yl]pyrrolo[2,3-b]pyridine (dDvas)

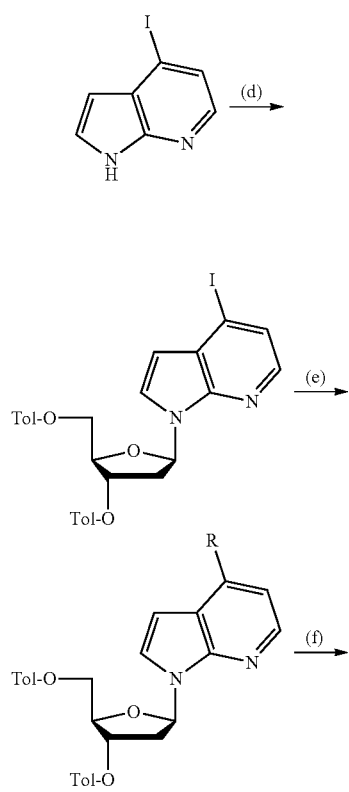

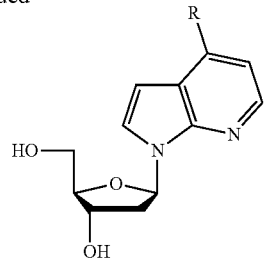

R represents a 2,2'-bithien-5-yl group, a 2-(2-thiazolyl)thien-5-yl group, or a 5-(2-thienyl)thiazol-2-yl group.

Reagents and Abbreviations:
(a) mCPBA, EtOAc, and then methanesulfonyl chloride and DMF;
(b) NaI CH$_3$COCl, and CH$_3$CN;
(c) NaH, 2-deoxy-3,5-di-O-p-toluoyl-α-D-erythro-pentofuranosyl chloride, and CH$_3$CN;
(d) dichlorobis(triphenylphosphine)palladium, a tributylstannyl derivative, and DMF; and
(e) NH$_3$, methanol or NaOMe, and methanol.

(3-1) Synthesis of 4-iodo-1H-pyrrolo[2,3-b]pyridine

A solution of meta-chlorobenzoic acid (14 g, 54 mmol) in ethyl acetate (30 mL) was dropwise added to a solution of 1H-pyrrolo[2,3-b]pyridine (5.3 g, 45 mmol) in ethyl acetate (45 mL) over 1 hr with stirring at 0° C. After completion of the dropping, the mixture was stirred at room temperature for 3 hr, followed by leaving to stand at 0° C. The resulting crystals were collected by filtration, washed with ethyl acetate, and then dried under reduced pressure. The crystals were dissolved in water (30 mL), and then 30% K$_2$CO$_3$ was added until the pH of the solution reached 10. The solution was left to stand at room temperature for 1 hr and then at 0° C. for 1 hr. The resulting precipitate was collected by filtration and was washed with ether to yield 3.5 g (58%) of N-oxide. The N-oxide (3.0 g, 22 mmol) was dissolved in DMF (16 mL). The resulting solution was heated at 50° C., and a solution of methanesulfonyl chloride (4.7 mL, 60 mmol) in DMF (6.4 mL) was dropwise added to the solution at 70° C. This reaction solution was stirred at 75° C. for 2 hr. The reaction solution was added to ice and was neutralized with 10 N NaOH at 0° C., followed by stirring at room temperature for 1 hr. The resulting precipitate was collected by filtration, washed with water, and dried at 60° C. under reduced pressure to yield 2.7 g (80%) of the target 4-chloro-1H-pyrrolo[2,3-b]pyridine. 4-Chloro-1H-pyrrolo[2,3-b]pyridine (2.7 g, 18 mmol) and NaI (13 g, 88 mmol) were dissolved in acetonitrile (28 mL), and CH$_3$COCl (3.5 mL, 50 mmol) was added thereto with stirring at room temperature. The reaction solution was heated at 85° C. for 12 hr and then cooled to room temperature, and 10% Na$_2$CO$_3$ (28 mL) and 10% NaHSO$_3$ (28 mL) were added thereto, followed by stirring at room temperature for 15 min. Ethyl acetate was added thereto for separation, and the organic layer was washed with saturated brine. The organic layer was dried over anhydrous sodium sulfate, concentrated, and purified with a silica gel column to yield 4-iodo-1-N-acetyl-pyrrolo[2,3-b]pyridine (2.0 g) and 4-iodo-1H-pyrrolo[2,3-b]pyridine (2.3 g). 4-Iodo-1-N-acetyl-pyrrolo[2,3-b]pyridine (2.0 g, 7.0 mmol) was dissolved in ethanol (70 mL) and refluxed in methanol containing 28% sodium methoxide (1.4 mL, 7.0 mmol) for 1 hr. The reaction solution was concentrated and separated between ethyl acetate and an aqueous saturated ammonium chloride solution. The organic layer was washed with an aqueous saturated ammonium chloride solution, dried over anhydrous sodium sulfate, concentrated, and then combined with 4-iodo-1H-pyrrolo[2,3-b]pyridine (2.3 g) obtained above. The mixture was recrystallized from ethanol to yield 4-iodo-1H-pyrrolo[2,3-b]pyridine (4.0 g, 92%).

4-Iodo-1H-pyrrolo[2,3-b]pyridine: $^1$H NMR (500 MHz, DMSO-$d_6$) δ 12.01 (s, 1H), 7.89 (d, 1H, J=5.0 Hz), 7.59 (t, 1H, J=3.1 Hz), 7.51 (d, 1H, J=5.0 Hz), 6.27 (d, 1H, J=3.4 Hz).

(3-2) Synthesis of 1-[2-deoxy-3,5-di-O-(toluoyl)-β-D-ribofuranosyl]-4-iodo-pyrrolo[2,3-b]pyridine NaH (156 mg, 60% dispersion in oil, 3.9 mmol) was added to a solution of 4-iodo-1H-pyrrolo[2,3-b]pyridine (950 mg, 3.9 mmol) in acetonitrile (39 mL). The mixture was stirred at room temperature for 1 hr, and 2-deoxy-3,5-di-O-p-toluoyl-α-D-erythropentofuranosyl chloride (1.8 g, 1.2 equivalent) was added thereto, followed by stirring at room temperature for 1.5 hr. The reaction solution was separated between ethyl acetate and an aqueous saturated ammonium chloride solution. The organic layer was washed with an aqueous saturated ammonium chloride solution and saturated brine, dried over anhydrous sodium sulfate, concentrated, and purified with a silica gel column to yield 1.8 g (77%) of 1-[2-deoxy-3,5-di-O-(toluoyl)-β-D-ribofuranosyl]-4-iodo-pyrrolo[2,3-b]pyridine.

(3-3) Synthesis of 1-[2-deoxy-β-D-ribofuranosyl]-4-(2,2'-bithien-5-yl)-pyrrolo[2,3-b]pyridine (dDsas)

A solution of 2-tributylstannyl-5,2-bithiophene (0.3 mmol), 1-[2-deoxy-3,5-di-β-(toluoyl)-β-D-ribofuranosyl]-4-iodo-pyrrolo[2,3-b]pyridine (120 mg, 0.2 mmol), and dichlorobistriphenylphosphine palladium (7 mg) in DMF (2 mL) was stirred at 100° C. for 1 hr. The reaction solution was separated between ethyl acetate and water, and the organic layer was washed with saturated brine, dried over anhydrous sodium sulfate, concentrated, and purified with a silica gel column to yield 1-[2-deoxy-3,5-di-O-(toluoyl)-β-D-ribofuranosyl]-4-(2,2'-bithien-5-yl)-pyrrolo[2,3-b]pyridine. This was dissolved in methylene chloride (10 mL) and methanol (2 mL), and 28% sodium methylate (0.12 mL) was added thereto, followed by stirring at room temperature for 30 min. 1-[2-Deoxy-β-D-ribofuranosyl]-4-(2,2'-bithien-5-yl)-pyrrolo[2,3-b]pyridine (dDsas, 54 mg, 68%) was obtained by purification with a silica gel column and by HPLC.

$^1$H NMR (300 MHz, DMSO-$d_6$) δ 8.26 (d, 1H, J=5.1 Hz), 7.88 (d, 1H, J=3.8 Hz), 7.80 (d, 1H, J=3.9 Hz), 7.58 (dd, 1H, J=1.1, 5.1 Hz), 7.44 (m, 3H), 7.14 (dd, 1H, J=3.7, 5.1 Hz), 6.96 (d, 1H, J=3.8 Hz), 6.75 (dd, 1H, J=6.1, 8.1 Hz), 5.26 (d, 1H, J=4.1 Hz), 5.00 (t, 1H, J=5.6 Hz), 4.39 (m, 1H), 3.84 (m, 1H), 3.56 (m, 2H), 2.59 (m, 1H), 2.23 (m, 1H).

(3-4) Synthesis of 1-[2-deoxy-β-D-ribofuranosyl]-4-[2-(2-thiazolyl)thien-5-yl]pyrrolo[2,3-b]pyridine (dDsav)

2-Tributylstannylthiophene (3.5 mL, 11 mmol) was added to a solution of 2-bromothiazole (0.9 mL, 10 mmol) and dichlorobistriphenylphosphine palladium (350 mg) in DMF (50 mL), followed by stirring at 90° C. for 3 hr. The reaction solution was concentrated and was separated between ethyl acetate and water. The organic layer was washed with saturated brine and dried over anhydrous sodium sulfate. The organic layer was concentrated and then purified with a silica gel column to yield 2,2'-thienylthiazole (1.4 g, 87%). A solution of 2,2'-thienylthiazole (251 mg, 1.5 mmol) in THF (15 mL) was cooled to −78° C., and n-butyllithium (0.96 mL, 1.5 mmol, 1.57 M solution in hexane) was added thereto, followed by stirring at −78° C. for 30 min. Trimethylsilyl chloride (1.5 mmol, 0.19 mL) was added thereto, followed by stirring at −78° C. for 30 min. Furthermore, n-butyllithium (0.96 mL, 1.5 mmol, 1.57 M solution in hexane) was added thereto, followed by stirring at −78° C. for 30 min, and then tributylstannyl chloride (0.45 mL, 1.6 mmol) was added thereto, followed by stirring at room temperature for 30 min. The reaction solution was separated between ethyl acetate and water, and the organic layer was washed with saturated brine, dried over anhydrous sodium sulfate, concentrated, and purified with a silica gel column to yield 2-tributylstannyl-5-(5'-trimethylsilyl-2-thienyl)thiophene (735 mg). 2-Tributylstannyl-5-(5'-trimethylsilyl-2-thienyl)thiophene (397 mg, 0.75 mmol) was added to a solution of 1-[2-deoxy-3,5-di-O-(toluoyl)-β-D-ribofuranosyl]-4-iodo-pyrrolo[2,3-b]pyridine (298 mg, 0.5 mmol) and dichlorobistriphenylphosphine palladium (18 mg, 0.025 mmol) in DMF (5 mL), followed by stirring at 100° C. for 1 hr. The reaction solution was separated between ethyl acetate and water, and the organic layer was washed with saturated brine, dried over anhydrous sodium sulfate, concentrated, and purified with a silica gel column to yield 1-[2-deoxy-3,5-di-O-(toluoyl)-β-D-ribofuranosyl]-4-(2-(5-(5'-trimethylsilyl-2-thienyl)thiophene)-pyrrolo[2,3-b]pyridine (335 mg). This was dissolved in methylene chloride (5 mL) and methanol (5 mL), and 28% sodium methylate (290 mg, 1.5 mmol) was added thereto, followed by stirring at room temperature for 30 min. Ammonium chloride (80 mg) was added to the reaction solution. After concentration, 1-[2-deoxy-β-D-ribofuranosyl]-4-[2-(2-thiazolyl)thien-5-yl]-pyrrolo[2,3-b]pyridine (dDsav, 112 mg) and 1-[2-deoxy-β-D-ribofuranosyl]-4-[2-(2-thienyl)thiazol-5-yl]pyrrolo[2,3-b]pyridine (dDv'as, 26 mg) were obtained by purification with a silica gel column and by HPLC.

dDsav: $^1$H NMR (300 MHz, DMSO-$d_6$) δ 8.30 (d, 1H, J=5.1 Hz), 7.91 (d, 1H, J=3.8 Hz), 7.87 (m, 2H), 7.79 (m, 2H), 7.48 (d, 1H, J=5.1 Hz), 6.96 (d, 1H, J=3.8 Hz), 6.76 (dd, 1H, 6.1, 8.0 Hz), 5.27 (d, 1H, J=4.1 Hz), 4.99 (t, 1H, J=5.6 Hz), 4.38 (m, 1H), 3.85 (m, 1H), 3.56 (m, 2H), 2.56 (m, 1H), 2.24 (m, 1H).

dDv'as: $^1$H NMR (300 MHz, DMSO-$d_6$) δ 8.51 (s, 1H), 8.30 (d, 1H, J=5.1 Hz), 7.93 (d, 1H, J=3.8 Hz), 7.79 (m, 2H), 7.47 (d, 1H, J=5.1 Hz), 7.22 (dd, 1H, J=4.0, 4.9 Hz), 7.94 (d, 1H, J=3.8 Hz), 6.75 (dd, 1H, J=6.2, 7.9 Hz), 5.27 (d, 1H, J=4.1 Hz), 4.99 (t, 1H, J=5.6 Hz), 3.38 (m, 1H), 3.59 (m, 2H), 2.57 (m, 1H), 2.24 (m, 1H).

(3-5) Synthesis of 1-[2-deoxy-β-D-ribofuranosyl]-4-[5-(2-thienyl)thiazol-2-yl]pyrrolo[2,3-b]pyridine (dDvas)

A solution of 5-(2-thienyl)thiazole (0.4 mmol) in diethyl ether was cooled to −78° C., and n-butyllithium (0.4 mmol, 1.57 M solution in hexane) was added thereto, followed by stirring at −78° C. for 30 min. Furthermore, tributylstannyl chloride was added thereto, followed by stirring at room temperature for 30 min. The reaction solution was separated between ethyl acetate and water. The organic layer was washed with saturated brine and concentrated, and 1-[2-deoxy-3,5-di-O-(toluoyl)-β-D-ribofuranosyl]-4-iodo-pyrrolo[2,3-b]pyridine (120 mg, 0.2 mmol), chlorobistriphenylphosphine palladium (5% mol), and DMF (2 mL) were added thereto, followed by stirring at 100° C. for 1 hr. The reaction solution was separated between ethyl acetate and water, and the organic layer was washed with saturated brine and water, dried over anhydrous sodium sulfate, and concentrated. After purification with a silica gel column and addition of sodium methoxide (1.6 mL), the resulting mixture was stirred at room temperature for 30 min. dDvas nucleoside (34 mg) was purified with a silica gel column and by HPLC.

dDvas: $^1$H NMR (300 MHz, DMSO-$d_6$) δ 8.37 (d, 1H, J=5.1 Hz), 8.31 (s, 1H), 7.96 (d, 1H, J=3.8 Hz), 7.68 (m, 2H), 7.54 (dd, 1H, J=1.1, 3.6 Hz), 7.19 (dd, 1H, 3.7, 5.1 Hz), 7.15 (d, 1H, J=3.7 Hz), 6.77 (dd, 1H, J=6.1, 8.0 Hz), 5.28 (d, 1H, J=4.1 Hz), 4.98 (t, 1H, J=5.5 Hz), 4.38 (m, 1H), 3.85 (m, 1H), 3.56 (m, 2H), 2.57 (m, 1H), 2.49 (m, 1H).

Example 4

Amidite Synthesis (dDss and dss)

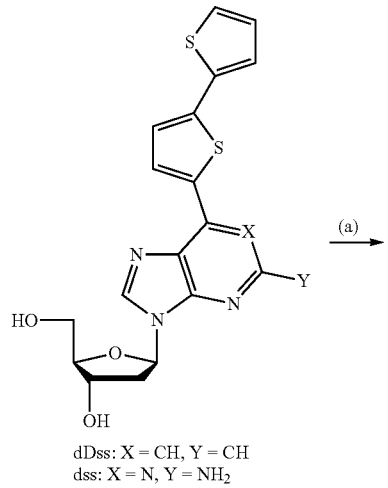

dDss: X = CH, Y = CH
dss: X = N, Y = NH$_2$

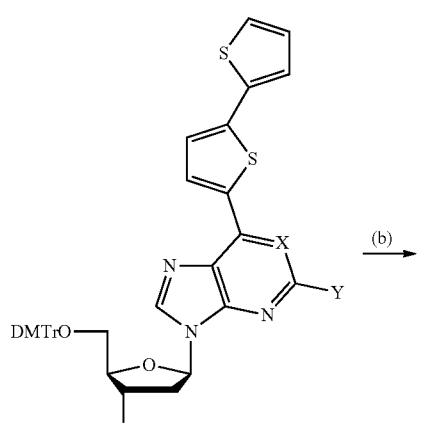

dDss: X = CH, Y = CH
dss: X = N, Y = NH-Pac

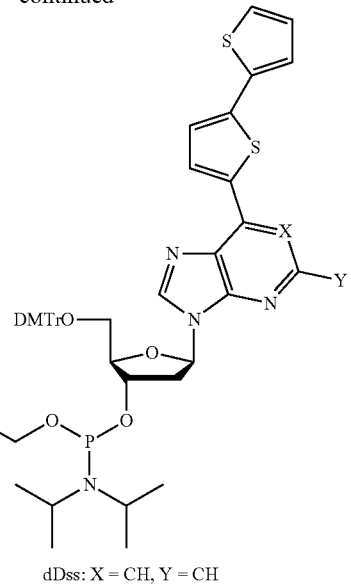

dDss: X = CH, Y = CH
dss: X = N, Y = NH-Pac

Conditions:
(a) DMTr-Cl, pyridine for dDss, trimethylsilyl chloride, phenoxyacetyl chloride, hydroxybenzotriazole, pyridine, and CH$_3$CN, and then DMTr-Cl and pyridine
(b) 2-cyanoethyl N,N-diisopropylaminochlorophosphoramidite, diisopropylamine, and THF.

(4-1) Synthesis of 7-(2,2'-bithien-5-yl)-3-(2-deoxy-5-O-(4,4'-dimethoxytrityl)-β-D-ribofuranosyl)imidazo[4,5-b]pyridine 7-(2,2'-Bithien-5-yl)-3-(2-deoxy-β-D-ribofuranosyl)imidazo[4,5-b]pyridine (dDss) (262 mg, 0.66 mmol) was azeotropically dried with pyridine three times and was then dissolved in pyridine (7.0 mL), and 4,4'-dimethoxytrityl chloride (367 mg, 0.79 mmol) was added thereto. The resulting mixture was stirred at room temperature for 1 hr and was then separated between ethyl acetate and an aqueous 5% sodium hydrogen carbonate solution. The organic layer was washed with saturated brine, dried over anhydrous sodium sulfate, and then concentrated under reduced pressure. 7-(2, 2'-Bithien-5-yl)-3-(2-deoxy-5-O-(4,4'-dimethoxytrityl)-β-D-ribofuranosyl)imidazo[4,5-b]pyridine (408 mg, 89%) was obtained through purification by silica gel column chromatography (elution with a solution of 1% methanol in methylene chloride).

$^1$H NMR (300 MHz, DMSO-$d_6$) δ 8.66 (s, 1H), 8.30 (d, 1H, J=5.2 Hz), 8.22 (d, 1H, J=3.9 hz), 7.67 (d, 1H, J=5.2 Hz), 7.60 (dd, 1H, J=1.1, 5.1 Hz), 7.48-7.46 (m, 2H), 7.34-7.31 (m, 2H), 7.24-7.14 (m, 8H), 6.80 (d, 2H, J=9.0 Hz), 6.75 (d, 2H, J=9.0 Hz), 6.55 (t, 1H, J=6.3 Hz), 5.39 (d, 1H, J=4.6 Hz), 4.51 (m, 1H), 3.70 and 3.67 (s, s, 6H), 3.19 (m, 2H), 2.96 (m, 1H), 2.41 (m, 1H).

HRMS (FAB, 3-NBA matrix) for C$_{40}$H$_{35}$N$_3$O$_5$S$_2$Na, (M+Na)$^+$ calculated value: 724.1916, observed value: 724.1978.

(4-2) Synthesis of 7-(2,2'-bithien-5-yl)-3-(2-deoxy-5-O-(4,4'-dimethoxytrityl)-β-D-ribofuranosyl)imidazo[4,5-b]pyridine 2-cyanoethyl-N,N-diisopropylaminophosphoramidite 7-(2,2'-Bithien-5-yl)-3-(2-deoxy-5-O-(4,4'-dimethoxytrityl)-β-D-ribofuranosyl)imidazo[4,5-b]pyridine (203 mg, 0.29 mmol) was azeotropically dried with pyridine three times and with THF three times. To this, diisopropylethylamine (76 μL, 0.43 mmol) and THF (1.5 mL) were added, and 2-cyanoethyl-N,N-diisopropylaminochlorophosphoramidite (78 μL, 0.35 mmol) was then added. The resulting mixture was stirred at room temperature for 1 hr. Methanol (50 μL) was added to the reaction solution, and the mixture was diluted with EtOAc:TEA (20:1, v/v, 20 mL), washed with an aqueous 5% sodium hydrogen carbonate solution and saturated brine, and then dried over anhydrous sodium sulfate. The organic layer was concentrated under reduced pressure. 7-(2,2'-Bithien-5-yl)-3-(2-deoxy-5-O-(4,4'-dimethoxytrityl)-β-D-ribofuranosyl)imidazo[4,5-b]pyridine 2-cyanoethyl-N,N-diisopropylaminophosphoramidite (260 mg, 99%) was obtained through purification by silica gel column chromatography (elution with a solution of methylene chloride containing 2% triethylamine:hexane (2:3)).

$^1$H NMR (300 MHz, CDCl$_3$) δ 8.33-8.30 (m, 2H), 8.11 (d, 1H, J=3.9 Hz), 7.47-7.41 (m, 3H), 7.35-7.17 (m, 10H), 7.07 (dd, 1H, J=3.6, 5.1 Hz), 6.82-6.76 (m, 4H), 6.62 (m, 1H), 4.80 (m, 1H), 4.34 (m, 1H), 3.91-3.78 (m, 10H), 3.49-3.32 (m, 2H), 2.94 (m, 1H), 2.73 (m, 1H), 2.64 (t, 1H, J=6.5 Hz), 2.48 (t, 1H, J=6.4 Hz), 1.23-1.12 (m, 12H).

$^{31}$P NMR (121 MHz, CDCl$_3$) δ 149.47 and 149.29 (diastereoisomer).

HRMS (FAB, 3-NBA matrix) for C$_{49}$H$_{52}$N$_5$O$_6$S$_2$PNa (M+Na)$^+$ calculated value: 924.2994, observed value: 924.3328.

(4-3) Synthesis of 2-phenoxyacetylamino-6-(2,2'-bithien-5-yl)-9-(2-deoxy-β-D-ribofuranosyl)purine 2-Amino-6-(2,2'-bithien-5-yl)-9-(2-deoxy-β-D-ribofuranosyl)purine (ss) (208 mg, 0.5 mmol) was azeotroped with pyridine three times and was dissolved in pyridine (2.5 mL), and trimethylsilyl chloride (476 μL, 3.8 mmol) was added thereto, followed by stirring at room temperature for 30 min (solution A). 1-Hydrorxybenzotriazole (122 mg, 0.9 mmol) was azeotroped with pyridine three times and was then dissolved in pyridine (0.25 mL) and acetonitrile (0.25 mL). The resulting solution was cooled to 0° C., and phenoxyacetyl chloride (104 μL, 0.75 mmol) was added thereto, followed by stirring for 5 min (solution B). Solution A was added to solution B at 0° C., and the mixture was stirred at room temperature for 12 hr. The reaction solution was cooled to 0° C., and 14% aqueous ammonia (0.5 mL) was added thereto, followed by stirring for 10 min. The reaction solution was separated between ethyl acetate and water, and the organic layer was dried over anhydrous sodium sulfate and was then concentrated. 2-Phenoxyacetylamino-6-(2,2'-bithien-5-yl)-9-(2-deoxy-β-D-ribofuranosyl)purine (246 mg, 89%) was obtained through purification by silica gel column chromatography (elution with a solution of 5% methanol in methylene chloride).

$^1$H NMR (300 MHz, DMSO) δ 10.77 (s, 1H), 8.74 (s, 1H), 8.55 (d, 1H, J=4.0 Hz), 7.65 (dd, 1H, J=1.1, 5.1 Hz), 7.54 (d, 1H, J=3.9 Hz), 7.51 (dd, 1H, J=1.1, 3.6 Hz), 7.34-7.29 (m, 2H), 7.17 (dd, 1H, J=5.7, 5.1 Hz), 7.01-6.94 (m, 3H), 6.41 (t, 1H, J=6.8 Hz), 5.35 (d, 1H, J=4.1 Hz), 5.10 (s, 2H), 4.93 (t, 1H, J=5.5 Hz), 4.46 (m, 1H), 3.89 (m, 1H), 3.59 (m, 2H), 2.79 (m, 1H), 2.35 (m, 1H).

(4-4) Synthesis of 2-phenoxyacetylamino-6-(2,2'-bithien-5-yl)-9-(2-deoxy-5-β-dimethoxytrityl-β-D-ribofuranosyl)purine 2-Phenoxyacetylamino-6-(2,2'-bithien-5-yl)-9-(2-deoxy-β-D-ribofuranosyl)purine (240 mg, 0.44 mmol) was azeotropically dried with pyridine and was then dissolved in pyridine (4.4 mL), and 4,4'-dimethoxytrityl chloride (163 mg, 0.48 mmol) was added thereto. The resulting mixture was stirred at room temperature for 1 hr and was then separated between ethyl acetate and an aqueous 5% sodium hydrogen carbonate solution. The organic layer was washed with saturated brine, dried over anhydrous sodium sulfate, and then concentrated under reduced pressure. 2-Phenoxyacetylamino-6-(2,2'-bithien-5-yl)-9-(2-deoxy-5-O-dimethoxytrityl-β-D-ribofuranosyl)purine (314 mg, 84%) was obtained through purification by silica gel column chromatography (elution with a solution of 5% methanol in methylene chloride).

$^1$H NMR (300 MHz, DMSO) δ10.72 (s, 1H), 8.64 (s, 1H), 8.56 (d, 1H, J=4.0 Hz), 7.65 (dd, 1H, J=1.1, 5.1 Hz), 7.55 (d, 1H, J=3.9 Hz), 7.52 (dd, 1H, J=1.1, 3.6 Hz), 7.34-7.27 (m, 4H), 7.19-7.12 (m, 8H), 7.00-6.95 (m, 3H), 6.75 (d, 2H, J=8.9 Hz), 6.69 (d, 2H, J=8.9 Hz), 6.45 (t, 1H, J=5.8 Hz), 5.33 (d, 1H, J=4.7 Hz), 5.05 (m, 2H), 4.55 (m, 1H), 4.01 (m, 1H), 3.67, 3.64 (s, s, 6H), 3.30 (m, 1H, overlapping with H$_2$O signal peak), 3.12 (m, 1H), 2.95 (m, 1H), 2.40 (m, 1H).

(4-5) Synthesis of 2-phenoxyacetylamino-6-(2,2'-bithien-5-yl)-9-(2-deoxy-5-β-dimethoxytrityl-β-D-ribofuranosyl)purine 2-cyanoethyl-N,N-diisopropylaminophosphoramidite 2-Phenoxyacetylamino-6-(2,2'-bithien-5-yl)-9-(2-deoxy-5-O-dimethoxytrityl-β-D-ribofuranosyl)purine (310 mg, 0.36 mmol) was azeotropically dried with pyridine three times and with THF three times. To this, diisopropylethylamine (95 μL, 0.55 mmol) and THF (1.8 mL) were added, and 2-cyanoethyl-N,N-diisopropylaminochlorophosphoramidite (98 μL, 0.44 mmol) was then added. The mixture was stirred at room temperature for 1 hr. Methanol (50 μL) was added to the reaction solution, and the resulting mixture was diluted with EtOAc:TEA (20:1, v/v, 20 mL), washed with an aqueous 5% sodium hydrogen carbonate solution and saturated brine, and then dried over anhydrous sodium sulfate. The organic layer was concentrated under reduced pressure. 2-Phenoxyacetylamino-6-(2,2'-bithien-5-yl)-9-(2-deoxy-5-O-dimethoxytrityl-β-D-ribofuranosyl)purine 2-cyanoethyl-N,N-diisopropylaminophosphoramidite (370 mg, 97%) was obtained through purification by silica gel column chromatography (elution with a solution of methylene chloride containing 2% triethylamine:hexane (2:3)).

$^1$H NMR (300 MHz, CDCl$_3$) δ 8.59, 8.58 (s, s, 1H), 8.22 (d, 1H, J=4.4 Hz), 7.39-7.17 (m, 14H), 7.13-7.05 (m, 4H), 6.82-6.75 (m, 4H), 6.50 (t, 1H, J=6.6 Hz), 4.94 (bs, 2H), 4.80 (m, 1H), 4.34 (m, 1H), 3.94-3.55 (m, 4H), 3.77 (s, 6H), 3.45-3.40 (m, 2H), 2.93 (m, 1H), 2.80-2.66 (m, 1H), 2.65 (t, 1H, J=6.4 Hz), 2.48 (t, 1H, J=6.4 Hz), 1.22-1.11 (m, 12H).

$^{31}$P NMR (121 MHz, CDCl$_3$) δ 149.57.

Example 5

Synthesis of deoxyribonucleoside 5'-triphosphate (dDssTP)

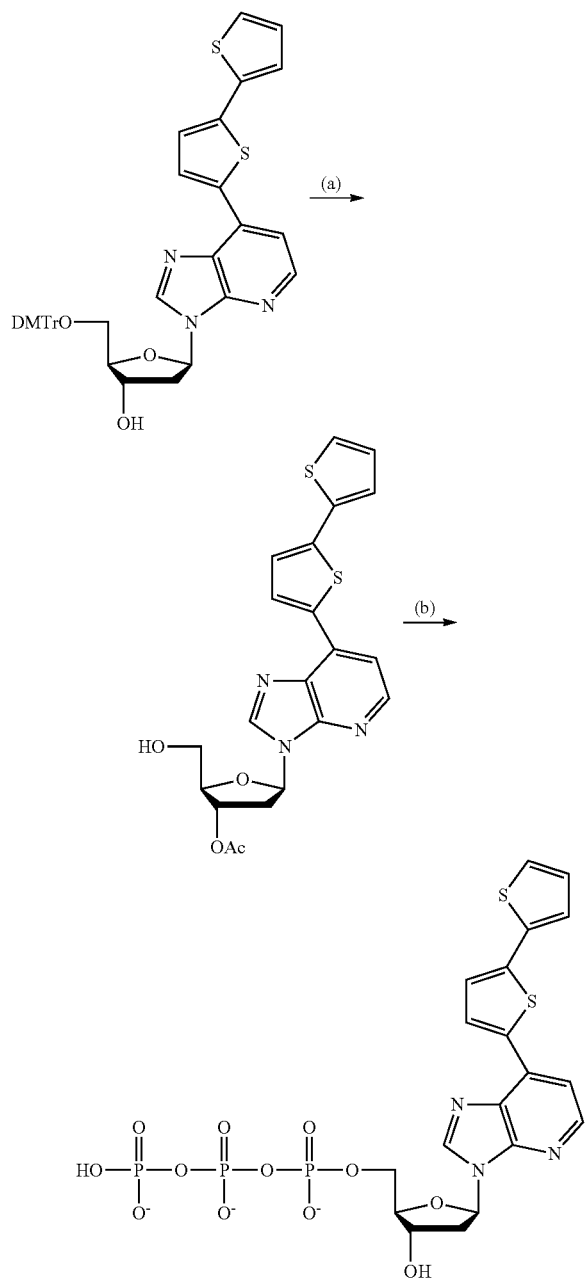

Conditions:
(a) acetic anhydride and pyridine, and then dichloroacetic acid and CH$_2$Cl$_2$;
(b) chloro-1,3,2-benzodioxaphosphorin-4-on, dioxane, pyridine, tri-n-butylamine, bis(tributylammonium)pyrophosphate, I$_2$, H$_2$O, 28% NH$_4$OH.

(5-1) Synthesis of 7-(2,2'-bithien-5-yl)-3-(2-deoxy-3-O-acetyl-β-D-ribofuranosyl)imidazo[4,5-b]pyridine 7-(2,2'-Bithien-5-yl)-3-(2-deoxy-5-O-(4,4'-dimethoxytrityl)-β-D-ribofuranosyl)imidazo[4,5-b]pyridine (195 mg, 0.28 mmol) was azeotropically dried with pyridine three times and was dissolved in pyridine (2.8 mL), and acetic anhydride (105 μL, 1.1 mmol) was added thereto, followed by stirring at room temperature for 12 hr. The reaction solution was separated between ethyl acetate and an aqueous 5% sodium hydrogen carbonate solution. The organic layer was washed with saturated brine, dried over anhydrous sodium sulfate, and then concentrated under reduced pressure. The residue was azeotropically dried with toluene and was then dissolved in methylene chloride (28 mL), and dichloroacetic acid (280 μL) was added thereto at 0° C., followed by stirring for 15 min. The reaction solution was separated with 5% sodium hydrogen carbonate. The organic layer was washed with an aqueous 5% sodium hydrogen carbonate solution and saturated brine, dried over anhydrous sodium sulfate, and then concentrated under reduced pressure. 7-(2,2'-Bithien-5-yl)-3-(2-deoxy-3-β-acetyl-β-D-ribofuranosyl)imidazo[4,5-b]pyridine (115 mg, 93%) was obtained through purification by silica gel column chromatography (elution with a solution of 1% methanol in methylene chloride).

$^1$H NMR (300 MHz, DMSO-d$_6$) δ 8.79 (s, 1H), 8.37 (d, 1H, J=4.7 Hz), 8.24 (d, 1H, J=3.9 Hz), 7.71 (d, 1H, J=5.2 Hz), 7.60 (dd, 1H, J=1.1, 5.1 Hz), 7.48 (m, 2H), 7.16 (dd, 1H, J=3.7, 5.1 Hz), 6.55 (dd, 1H, J=5.9, 8.7 Hz), 5.41 (d, 1H, J=5.8 Hz), 5.31 (t, 1H, J=5.2 Hz), 4.13 (m, 1H), 3.71-3.63 (m, 10H), 3.71-3.63 (m, 2H), 3.06 (m 1H), 2.53 (m, 1H), 2.11 (s, 3H).

HRMS (FAB, 3-NBA matrix) for C$_{21}$H$_{20}$N$_3$O$_4$S$_2$ (M+H)$^+$ calculated value: 442.0895, observed value: 442.0869.

(5-2) Synthesis of 7-(2,2'-bithien-5-yl)-3-(2-deoxy-β-D-ribofuranosyl)imidazo[4,5-b]pyridine 5'-triphosphate 7-(2,2'-Bithien-5-yl)-3-(2-deoxy-3-O-acetyl-β-D-ribofuranosyl)imidazo[4,5-b]pyridine (44 mg, 0.1 mmol) was azeotropically dried with pyridine and was then dissolved in pyridine (100 μL) and dioxane (100 μL). A solution of 1 M 2-chloro-1,3,2-benzodioxaphosphorin-4-one in dioxane (110 μL, 0.11 mmol) was added thereto, followed by stirring for 10 min. To this solution, a solution of tributylamine (100 μL) and a solution of bis(tributylammonium)pyrophosphate in 0.5 M DMF (300 μL, 0.15 mmol) was added, followed by stirring at room temperature for 10 min. A solution of 1% iodine in pyridine/water (98:2, v/v, 2.0 mL) was added thereto, followed by stirring for 15 min, and an aqueous 5% sodium hydrogen sulfite solution (150 μL) was added thereto. Water (5.0 mL) was further added thereto, followed by stirring for 30 min. Then, 28% aqueous ammonia (20 mL) was added thereto, followed by stirring at room temperature for 4 hr. The reaction solution was concentrated under reduced pressure, and 7-(2,2'-bithien-5-yl)-3-(2-deoxy-β-D-ribofuranosyl)imidazo[4,5-b]pyridine 5'-triphosphate (33 μmol, 33%) was obtained through purification by DEAE Sephadex (A-25) column chromatography (elution with a solution of 50 mM to 1.0 M TEAB) and C18-HPLC (elution with 0% to 50% acetonitrile in 100 mM TEAA).

$^1$H NMR (300 MHz, D$_2$O) δ 8.49 (s, 1H), 8.08 (d, 1H, J=5.4 Hz), 7.58 (d, 1H, J=4.0 Hz), 7.33-7.30 (m, 2H), 7.06 (dd, 1H, J=1.1, 4.7 Hz), 6.99 (dd, 1H, J=3.7, 5.1 Hz), 6.91 (d, 1H, J=3.9 Hz), 6.29 (t, 1H, J=6.9 Hz), 4.68 (m, 1H, overlapping with D$_2$O), 4.18 (m, 1H), 4.10-4.02 (m, 2H), 3.05 (q, 22H, J=7.3 Hz), 2.68 (m, 1H), 2.41 (m, 1H), 1.14 (t, 34H, J=7.3 Hz).

$^{31}$P NMR (121 MHz, D$_2$O) δ -9.71 (d, 1P, J=19.8 Hz), -10.72 (d, 1P, J=19.8 Hz), -22.54 (t, 1P, J=20.0 Hz).

UV-vis spectral data in 10 mM sodium phosphate buffer (pH 7.0): λmax=264 nm (ε 9900), 368 nm (ε 31400).

ESI-MS ($C_{19}H_{20}N_3O_{12}S_2P_3$); calculated value: 637.96 (M−H)⁻, observed value: 637.87 (M−H)⁻.

Example 6

Synthesis of ribonucleoside 5′-triphosphate (DssTP)

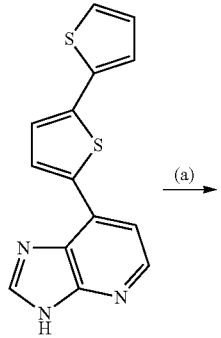

(a)

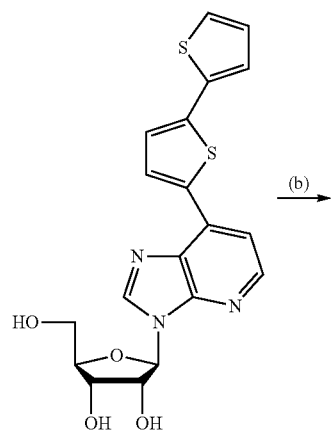

(b)

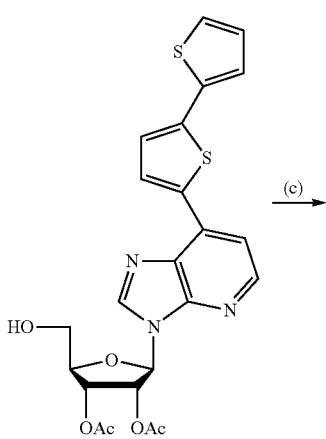

(c)

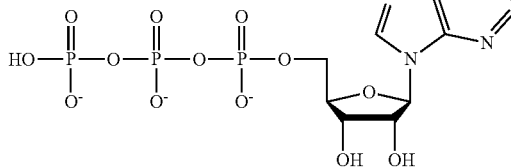
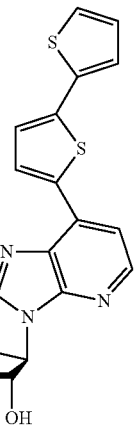

Conditions:
(a) tetra-O-acetyl-β-D-ribofuranose and chloroacetic acid;
(b) (i) DMTrCl and pyridine; (ii) acetic anhydride and pyridine, and then dichloracetic acid and CH₂Cl₂;
(c) 2-chloro-4H-1,3,2-benzolioxaphospholin-4-one, dioxane, pyridine, tri-n-butylamine, bis(tri-n-butylammonium)pyrophosphate, and DMF, and then I₂/pyridine/H₂O.

(6-1) Synthesis of 7-(2,2′-bithien-5-yl)-3-(β-D-ribofuranosyl)imidazo[4,5-b]pyridine 7-(2,2′-Bithien-5-yl)-3H-imidazo[4,5-b]pyridine (566 mg, 2.0 mmol), tetra-O-acetyl-β-D-ribofuranose (700 mg, 2.2 mmol), and chloroacetic acid (12 mg) were molten at 200° C. for 10 min. After cooling, the mixture was dissolved in methylene chloride and methanol (1:1, v/v, 16 mL), and a solution of 28% sodium methoxide in methanol (2.0 mL) was added thereto, followed by stirring at room temperature for 30 min. The reaction solution was concentrated under reduced pressure, and 7-(2,2′-bithien-5-yl)-3-(β-D-ribofuranosyl)imidazo[4,5-b]pyridine (190 mg, 23%) was obtained through purification by silica gel column chromatography (elution with a solution of 5% methanol in methylene chloride) and C18-HPLC.

¹H NMR (300 MHz, DMSO-$d_6$) δ 8.80 (s, 1H), 8.36 (d, 1H, J=5.2 Hz), 8.24 (d, 1H, J=3.9 Hz), 7.70 (d, 1H, J=5.2 Hz), 6.60 (dd, 1H, J=1.0, 5.1 Hz), 7.49-7.46 (m, 2H), 7.16 (dd, 1H, J=3.7, 5.1 Hz), 6.09 (d, 1H, J=5.7 Hz), 5.51 (d, 1H, J=6.0 Hz), 5.26 (dd, 1H, J=5.0, 6.4 Hz), 5.21 (d, 1H, J=4.9 Hz), 4.68 (m, 1H), 4.20 (m, 1H), 3.75-3.55 (m, 2H).

¹³C NMR (75 MHz, DMSO-$d_6$) δ 147.25, 144.04, 143.94, 140.10, 136.09, 135.43, 131.58, 130.89, 130.03, 128.57, 126.27, 124.78, 124.57, 113.60, 87.83, 85.57, 73.49, 79.41, 61.41.

HRMS (FAB, 3-NBA matrix) for $C_{19}H_{18}N_3O_4S_2$, (M+H)⁺ calculated value: 416.0739, observed value: 416.0755. ESI-MS ($C_{19}H_{17}N_3O_4S_2$); calculated value: 416.07 (M+H)⁺, observed value: 415.86 (M+H)⁺.

(6-2) Synthesis of 7-(2,2′-bithien-5-yl)-3-(2,3-di-O-acetyl-β-D-ribofuranosyl)imidazo[4,5-b]pyridine 7-(2,2′-Bithien-5-yl)-3-(β-D-ribofuranosyl)imidazo[4,5-b]pyridine (166 mg, 0.4 mmol) was azeotropically dried with pyridine three times and was then dissolved in pyridine (4.0 mL), and 4,4′-dimethoxytrityl chloride (162 mg, 0.48 mmol) was added thereto. After stirring at room temperature for 1 hr, the solution was separated between ethyl acetate and 5% sodium hydrogen carbonate, and the organic layer was washed with water and saturated brine and was concentrated under reduced pressure. The dimethoxytrityl form was purified by silica gel column chromatography (elution with a solution of 1% methanol in methylene chloride) and was azeotropically dried with pyridine three times. Pyridine (4 mL) was added thereto, and acetic anhydride (151 μL, 1.6 mmol) was further added thereto, followed by stirring at room temperature for 12 hr. The reaction solution was separated between ethyl acetate and 5% sodium hydrogen carbonate, and the organic layer was washed with water and saturated brine, dried over anhydrous sodium sulfate, and concentrated under reduced pressure. After azeotropic drying with toluene, the resulting substance was dissolved in methylene chloride (40 mL), and dichloroacetic acid (400 μL) was added thereto at 0° C., followed by stirring for 15 min. The reaction solution was separated with 5% sodium hydrogen carbonate, and the organic layer was washed with an aqueous 5% sodium hydrogen carbonate solution and saturated brine, dried over anhydrous sodium sulfate, and concentrated under reduced pressure. 7-(2,2'-Bithien-5-yl)-3-(2,3-di-O-acetyl-β-D-ribofuranosyl)imidazo[4,5-b]pyridine (178 mg, 89%) was obtained through purification by silica gel column chromatography (elution of 0.5% methanol in methylene chloride).

$^1$H NMR (300 MHz, DMSO-$d_6$) δ 8.83 (s, 1H), 8.38 (d, 1H, J=5.3 Hz), 8.25 (d, 1H, J=4.0 Hz), 7.73 (d, 1H, J=5.3 Hz), 7.61 (dd, 1H, J=1.1, 5.1 Hz), 7.50-7.47 (m, 2H), 7.16 (dd, 1H, J=3.7, 5.1 Hz), 6.39 (d, 1H, J=6.7 Hz), 6.04 (dd, 1H, J=5.7, 6.6 Hz), 5.58-5.53 (m, 2H), 4.28 (m, 1H), 3.81-3.63 (m, 2H) 2.15 (s, 3H), 2.00 (s, 3H).

HRMS (FAB, 3-NBA matrix) for $C_{23}H_{22}N_3O_6S_2$, $(M+H)^+$ calculated value: 500.0950, observed value: 500.0929.

(6-3) Synthesis of 7-(2,2'-bithien-5-yl)-3-(β-D-ribofuranosyl)imidazo[4,5-b]pyridine 5'-triphosphate 7-(2,2'-Bithien-5-yl)-3-(3-O-acetyl-β-D-ribofuranosyl) imidazo[4,5-b]pyridine (50 mg, 0.1 mmol) was azeotropically dried with pyridine and was then dissolved in pyridine (100 μL) and dioxane (100 μL), and a solution of 1 M 2-chloro-1,3,2-benzodioxaphosphorin-4-one in 1 M dioxane (110 μL, 0.11 mmol) was added thereto, followed by stirring for 10 min. To this solution, a solution of tributylamine (100 μL) and a solution of bis(tributylammonium)pyrophosphate in 0.5 M DMF (300 μL, 0.15 mmol) was added, followed by stirring at room temperature for 10 min. A solution of 1% iodine in pyridine/water (98:2, v/v, 2.0 mL) was added thereto, followed by stirring for 15 min, and an aqueous 5% sodium hydrogen sulfite solution (150 μL) was added thereto. Water (5.0 mL) was further added thereto, followed by stirring for 30 min. Then, 28% aqueous ammonia (20 mL) was added thereto, followed by stirring at room temperature for 4 hr. The reaction solution was concentrated under reduced pressure, and 7-(2,2'-bithien-5-yl)-3-(β-D-ribofuranosyl) imidazo[4,5-b]pyridine 5'-triphosphate (26 μmol, 26%) was obtained through purification by DEAE Sephadex (A-25) column chromatography (elution with a solution of 50 mM to 1.0 M TEAB and a solution of 10% acetonitrile in 1 M TEAB) and C18-HPLC (elution with 0% to 50% acetonitrile in 100 mM TEAA).

$^1$H NMR (300 MHz, D$_2$O) δ 8.64 (s, 1H), 8.14 (d, 1H, J=5.4 Hz), 7.75 (d, 1H, J=4.0 Hz), 7.44 (d, 1H, J=5.4 Hz), 7.30 (dd, 1H, J=1.1, 5.1 Hz), 7.15 (dd, 1H, J=1.1, 3.6 Hz), 7.10 (d, 1H, J=3.9 Hz), 6.97 (dd, 1H, J=3.7, 5.1 Hz), 6.12 (d, 1H, J=5.7 Hz), 4.74 (m, 1H, overlapping with D$_2$O), 4.53 (m, 1H), 4.33 (m, 1H), 4.26-4.12 (m, 2H), 3.08 (q, 26H, J=7.4 Hz), 1.16 (t, 38H, J=7.3 Hz).

$^{31}$P NMR (121 MHz, D$_2$O) δ -9.56 (d, 1P, J=19.7 Hz), -10.69 (d, 1P, J=20.0 Hz), -22.44 (t, 1P, J=20.0 Hz).

UV-vis spectral data in 10 mM sodium phosphate buffer (pH 7.0): λmax=264 nm (ε 10100), 368 nm (ε 31800).

ESI-MS ($C_{19}H_{20}N_3O_{13}S_2P_3$); calculated value: 653.96 $(M-H)^-$, observed value: 653.99 $(M-H)^-$.

Example 7

Synthesis of ribonucleoside 5'-triphosphate (ssTP)

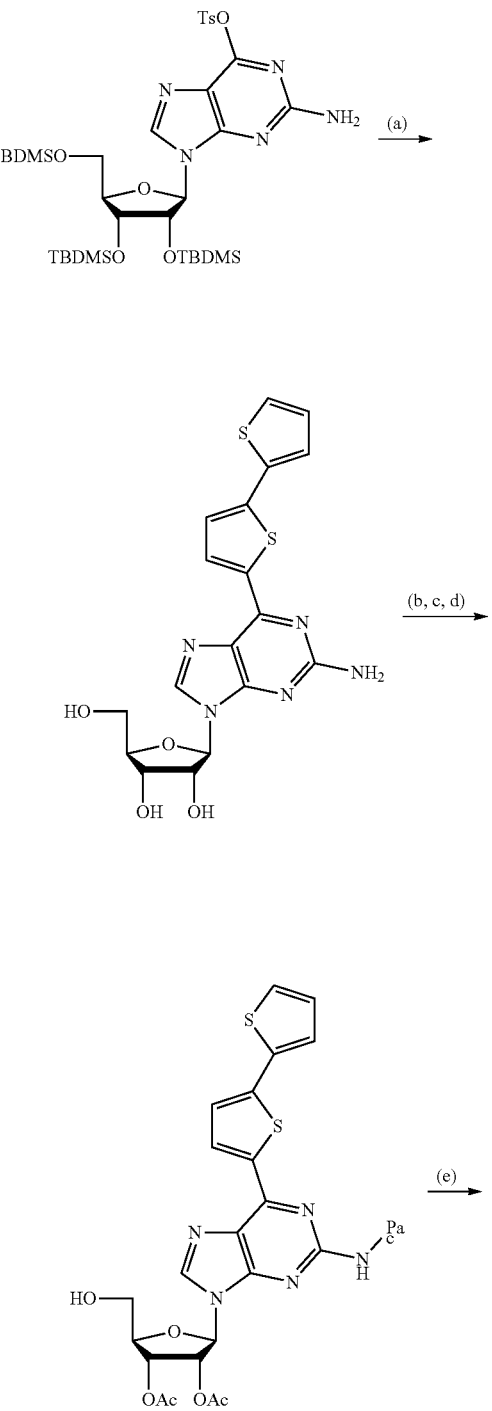

-continued

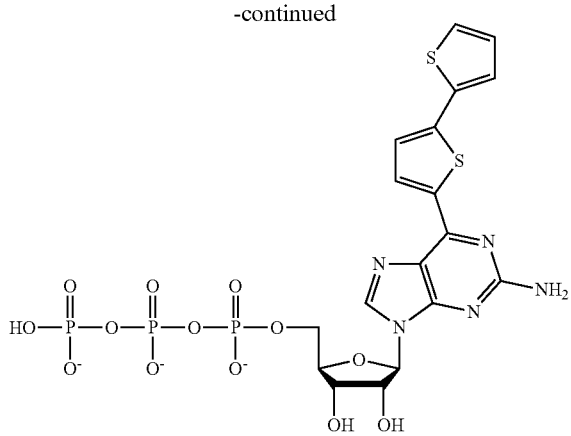

Conditions:
(a) 5-tributylstannyl-2,2'-bithiophene, Pd(PPh₃)₄, LiCl, and dioxane, and then TBAF and THF;
(b) trimethylsilyl chloride, phenoxyacetyl chloride, hydroxy-benzotriazole, pyridine, and CH₃CN, and then DMTr-Cl and pyridine;
(c) acetic anhydride and pyridine;
(d) dichloroacetic acid and CH₂Cl₂; (e) chloro-1,3,2-benzodioxaphosphorin-4-on, dioxane, pyridine, tri-n-butylamine, bis(tributylammonium)pyrophosphate, I₂, H₂O, and 28% NH₄OH.

(7-1) Synthesis of 2-amino-6-(2,2'-bithien-5-yl)-9-(β-D-ribofuranosyl)purine (ss)

A solution of 6-O-tosyl-2',3',5'-tri-O-tert-butyldimethylsilyl-guanosine (780 mg, 1.0 mmol), tetrakis(triphenylphosphine)palladium (58 mg, 0.05 mmol), lithium chloride (84 mg, 2.0 mmol), and 5-tributylstannyl-2,2'-bithiophene (5.0 mmol) in dioxane was refluxed at 120° C. for 5 hr. The reaction solution was separated between ethyl acetate and water, and the organic layer was washed with water, dried over anhydrous sodium sulfate, and concentrated under reduced pressure. 2',3',5'-Tri-O-tert-butyldimethylsilyl-2-amino-6-(2,2'-bithien-5-yl)-9-(β-D-ribofuranosyl)purine was purified by silica gel column chromatography (elution with methylene chloride). A solution of 1 M tetrabutylammonium fluoride in THF solution (4.5 mL) was added to a solution of 2',3',5'-tri-O-ter-butyldimethylsilyl-2-amino-6-(2,2'-bithien-5-yl)-9-(3-D-ribofuranosyl)purine in THF (5.5 mL), followed by stirring at room temperature for 30 min. The reaction solution was concentrated, and then 2-amino-6-(2,2'-bithien-5-yl)-9-(β-D-ribofuranosyl)purine (391 mg, 90%, second stage yield) was obtained through purification by silica gel column chromatography and RP-HPLC.

¹H NMR (300 MHz, DMSO-d₆) δ 8.46 (d, 1H, J=3.9 Hz), 8.41 (s, 1H), 7.61 (dd, 1H, J=1.1, 5.1 Hz), 7.49-7.46 (m, 2H), 7.16 (dd, 1H, J=3.7, 5.1 Hz), 6.58 (bs, 2H), 5.87 (d, 1H, J=5.9 Hz), 5.47 (d, 1H, J=5.9 Hz), 5.47 (d, 1H, J=6.0 Hz), 5.17 (d, 1H, J=4.8 Hz), 5.08 (t, 1H, J=5.6 Hz), 4.53 (m, 1H), 4.15 (m, 1H), 3.93 (m, 1H), 3.70-3.53 (m, 2H).

(7-2) Synthesis of 2-phenoxyacetylamino-6-(2,2'-bithien-5-yl)-9-(2',3'-di-O-acetyl-β-D-ribofuranosyl)purine 2-Amino-6-(2,2'-bithien-5-yl)-9-(β-D-ribofuranosyl)purine (216 mg, 0.5 mmol) was azeotroped with pyridine three times and was dissolved in pyridine (2.5 mL), and trimethylsilyl chloride (635 μL, 5.0 mmol) was added thereto, followed by stirring at room temperature for 30 min (solution A). 1-Hydrorxybenzotriazole (122 mg, 0.9 mmol) was azeotroped with pyridine three times and was then dissolved in pyridine (0.25 mL) and acetonitrile (0.25 mL). The resulting solution was cooled to 0° C., and phenoxyacetyl chloride (104 μL, 0.75 mmol) was added thereto, followed by stirring for 5 min (solution B). Solution A was added to solution B at 0° C., and the mixture was stirred at room temperature for 12 hr. The reaction solution was cooled to 0° C., and 14% aqueous ammonia (0.5 mL) was added thereto, followed by stirring for 10 min. The reaction solution was separated between ethyl acetate and water, and the organic layer was dried over anhydrous sodium sulfate and was then concentrated. 2-Phenoxyacetylamino-6-(2,2'-bithien-5-yl)-9-(β-D-ribofuranosyl)purine (230 mg, 81%) was obtained through purification by silica gel column chromatography (elution with a solution of 5% methanol in methylene chloride). 2-Phenoxyacetylamino-6-(2,2'-bithien-5-yl)-9-(β-D-ribofuranosyl)purine (230 mg, 0.4 mmol) was azeotropically dried with pyridine and was dissolved in pyridine (4.0 mL), and 4,4'-dimethoxytrityl chloride (152 mg, 0.44 mmol) was added thereto. After stirring at room temperature for 1 hr, the solution was separated between ethyl acetate and an aqueous 5% sodium hydrogen carbonate solution. The organic layer was washed with water and saturated brine, dried over anhydrous sodium sulfate, and concentrated under reduced pressure. 2-Phenoxyacetylamino-6-(2,2'-bithien-5-yl)-9-(5-O-dimethoxytrityl-β-D-ribofuranosyl)purine (228 mg, 65%) was obtained through purification by silica gel column chromatography (elution with a solution of 1% methanol in methylene chloride). 2-Phenoxyacetylamino-6-(2,2'-bithien-5-yl)-9-(5-O-dimethoxytrityl-β-D-ribofuranosyl)purine (228 mg, 0.26 mmol) was azeotropically dried with pyridine three times and was then dissolved in pyridine (2.6 mL), and acetic anhydride (99 μL, 1.0 mmol) was added thereto, followed by stirring at room temperature for 12 hr. The reaction solution was separated between ethyl acetate and 5% sodium hydrogen carbonate, and the organic layer was washed with water and saturated brine, dried over anhydrous sodium sulfate, and concentrated under reduced pressure. After azeotropic drying with toluene, the resulting substance was dissolved in methylene chloride (26 mL), and dichloroacetic acid (260 μL) was added thereto at 0° C., followed by stirring for 15 min. The reaction solution was separated with 5% sodium hydrogen carbonate, and the organic layer was washed with an aqueous 5% sodium hydrogen carbonate solution and saturated brine, dried over anhydrous sodium sulfate, and concentrated under reduced pressure. 2-Phenoxyacetylamino-6-(2,2'-bithien-5-yl)-9-(2',3'-di-O-acetyl-β-D-ribofuranosyl)purine (134 mg, 79%, second stage yield) was obtained through purification by silica gel column chromatography (elution of 0.5% methanol in methylene chloride).

¹H NMR (300 MHz, DMSO-d₆) δ10.83 (s, 1H), 8.80 (s, 1H), 8.55 (d, 1H, J=1H), 7.66 (d, 1H, J=5.1 Hz), 7.56 (d, 1H, J=4.0 Hz), 7.52 (d, 1H, J=3.5 Hz), 7.32 (m, 2H), 7.18 (m, 1H), 7.02-6.95 (m, 3H), 6.27 (d, 1H, J=6.5 Hz), 5.92 (t, 1H, J=6.2 Hz), 5.57 (dd, 1H, J=2.9, 5.6 Hz), 5.33 (t, 1H, J=5.4 Hz), 5.10 (s, 2H), 4.26 (m, 1H), 3.73 (m, 2H), 2.14 (s, 3H), 1.99 (s, 3H).

(7-3) Synthesis of 2-phenoxyacetylamino-6-(2,2'-bithien-5-yl)-9-(β-D-ribofuranosyl)purine 5'-triphosphate 2-Phenoxyacetylamino-6-(2,2'-bithien-5-yl)-1-(2',3'-di-O-acetyl-β-D-ribofuranosyl)purine (65 mg, 0.1 mmol) was azeotropically dried with pyridine and was then dissolved in pyridine (100 μL) and dioxane (300 μL), and a solution of 2-chloro-1,3,2-benzodioxaphosphorin-4-one in 1 M dioxane (110 μL, 0.11 mmol) was added thereto, followed by stirring for 10 min. To this solution, a solution of tributylamine (100

µL) and a solution of bis(tributylammonium)pyrophosphate in 0.5 M DMF (300 µL, 0.15 mmol) were added, followed by stirring at room temperature for 10 min. A solution of 1% iodine in pyridine/water (98:2, v/v, 2.0 mL) was added thereto, followed by stirring for 15 min, and an aqueous 5% sodium hydrogen sulfite solution (150 µL) was added thereto. Water (5.0 mL) was further added thereto, followed by stirring for 30 min. Then, 28% aqueous ammonia (20 mL) was added thereto, followed by stirring at 55° C. for 3 hr. The reaction solution was concentrated under reduced pressure, and 2-phenoxyacetylamino-6-(2,2'-bithien-5-yl)-9-(β-D-ribofuranosyl)purine 5'-triphosphate (27.6 mmol, 27%) was obtained through purification by DEAE Sephadex (A-25) column chromatography (elution with a solution of 50 mM to 1.0 M TEAB and a solution of 10% acetonitrile in 1 M TEAB) and C18-HPLC.

$^1$H NMR (300 MHz, D$_2$O) δ 8.42 (s, 1H), 8.10 (d, 1H, J=4.0 Hz), 7.36 (d, 1H, J=5.0 Hz), 7.24 (d, 2H, J=3.9 Hz), 7.01 (dd, 1H, J=3.8, 5.0 Hz), 6.00 (d, 1H, J=5.9 Hz), 4.86 (m, 1H), 4.64 (m, 1H), 4.41 (m, 1H), 4.29 (m, 2H), 3.19 (q, 25H, J=7.4 Hz), 1.28 (t, 37H, J=7.3 Hz).

$^{31}$P NMR (121 MHz, D$_2$O) 8-9.28 (d, 1P, J=19.4 Hz), −10.70 (d, 1P, J=19.7 Hz), −22.41 (t, 1P, J=20.0 Hz).

UV-vis spectral data in 10 mM sodium phosphate buffer (pH 7.0): Amax=388 nm (E 32500).

ESI-MS (C$_{18}$H$_{20}$N$_5$O$_{13}$S$_2$P$_3$); calculated value: 669.97 (M−H)$^-$, observed value: 669.39 (M−H)$^-$.

Example 8

Fluorescence Characteristics of Nucleoside Derivative of Unnatural Fluorescent Base Fluorescence characteristics of nucleosides including an unnatural base, ss, sss, Dss, Dsss, Dsas, Dsav, or Dvas, were evaluated. For comparison, fluorescence characteristics of nucleosides including known unnatural bases, 2-aminopurine, s (2-amino-6-(2-thienyl)purin-9-yl group), v (2-amino-6-(2-thiazolyl)purin-9-yl group), and Ds (7-(2-thienyl)imidazo[4,5-b]pyridin-3-yl group) were also evaluated. FIG. 1 shows the structures of deoxyribonucleoside derivatives, and Table 1 shows the fluorescence characteristics thereof.

The fluorescent ds has a short excitation wavelength of 350 nm, and the fluorescence intensity of ds is also low (ε×φ=2576). The dv emits fluorescence by excitation at a wavelength of 363 nm, but its nucleoside derivative shows low stability under basic conditions. The dDs emits fluorescence by excitation at a wavelength of about 310 nm, but does not emit light by excitation at a wavelength of 350 nm or more. Known 2-aminopurine emits fluorescence by excitation at a wavelength of about 300 nm, but the fluorescence intensity emitted by excitation at a wavelength of 350 nm or more is considerably low.

Contrarily, the dss emits strong fluorescence (ε×φ=9072) by excitation at a wavelength of 388 nm, and the dDss emits further strong fluorescence (ε×φ=10400) by excitation at a wavelength of 371 nm.

FIG. 2 shows fluorescence and its spectra of ribonucleoside triphosphate derivatives (substrates for transcription) including an unnatural base, s, Dss, or ss. The nucleotide having an unnatural base Dss or ss showed fluorescence stronger than that of the nucleotide having an unnatural base s.

Thus, it has been revealed that the unnatural base of the present invention, in which two or more heterocyclic moieties are linked together at the 6-position (the 6-position of purine ring) of a purine base, 1-deazapurine, or 1,7-deazapurine, has superior fluorescence characteristics to existing unnatural bases.

Example 9

Incorporation of Unnatural Fluorescent Base Substrate into DNA by Replication As an example of incorporation of an unnatural fluorescent base substrate into DNA by replication, an experiment of incorporation of Dss into DNA by replication using a Klenow fragment (exo+) was performed.

Template strand DNA (SEQ ID NO: 1,35-mer, 400 nM) dissolved in 2× reaction buffer (20 mM tris-HCl, pH 7.5, 14 mM MgCl$_2$, 0.2 mM DTT) and a primer labeled with $^{32}$P at the 5'-end (SEQ ID NO: 2,23-mer, 400 nM) were heated at 95° C. for 3 min and then slowly cooled for annealing to form a double strand. To each 5 µL of the resulting double-stranded DNA solution, 2.5 µL of a 4×dNTP solution mixture (40 µM dTTP, 40 µM dCTP, 0 to 40 µM dDssTP) and 2.5 µL (1 unit) of Klenow fragment (Takara Shuzo Co., Ltd.) diluted with water were added to start the enzyme reaction at 37° C. After incubation at 37° C., the reaction was terminated by addition of a TBE solution containing 10 µL of 10 M urea and heating at 75° C. for 3 min. A part of the reaction solution was subjected to electrophoresis with 15% polyacrylamide-7 M urea gel and analyzed with a bio-imaging analyzer (FLA7000, Fujifilm Corporation).

TABLE 1

Fluorescence characteristics of base analog nucleoside

| Base analog | Absorption maximum (nm) | Molar absoption coefficient ε (M$^{-1}$cm$^{-1}$) | Excitation wavelength (nm) | Fluorescence wavelength (nm) | Stokes shift (nm) | Quantum yield (φ) | Fluorescence intensity (ε × φ) |
|---|---|---|---|---|---|---|---|
| ds | 353 | 11200 | 351 | 429 | 78 | 0.23 | 2576 |
| dv | 363 | 8400 | 357 | 461 | 104 | 0.41 | 3444 |
| dDs | 313 | 22000 | 312 | 366 | 54 | 0.19 | 4180 |
| dss | 388 | 37800 | 388 | 457 | 69 | 0.24 | 9072 |
| dsss | 414 | 44800 | 419 | 508 | 89 | 0.11 | 4928 |
| dDss | 370 | 32500 | 371 | 442 | 71 | 0.32 | 10400 |
| dDsss | 403 | 34800 | 407 | 489 | 82 | 0.09 | 3132 |
| dDsas | 365 | 21500 | 367 | 451 | 84 | 0.13 | 2795 |
| dDsav | 365 | 21500 | 368 | 445 | 77 | 0.13 | 2795 |
| dDvas | 377 | 27000 | 378 | 449 | 71 | 0.14 | 3780 |
| 2-aminoprine[1] | 304 | 7100 | 303 | 370 | 67 | 0.68 | 4828 |

[1]Fluorescence studies of nucleotides and polynucleotides. D. C. Ward, et al., J. Biol. Chem., 244, 1228-1237 (1969).

Use of an unnatural base pair Dss-Pa (pyrrolo-2-carbaldehyde) allowed incorporation of dDssTP into a specific position (the position complements the Pa in the template DNA) in the extended DNA strand in replication using the Klenow fragment of *Escherichia coli*, in which DNA containing Pa base complementary to Dss is used as a template (FIG. 3).

In the electrophoresis photograph in FIG. 3, the band shown as 33-mer is a completely extended DNA fragment. It is revealed that Dss nucleotide is efficiently incorporated into DNA by reducing the amount of the substance of the unnatural fluorescent base (dDssTP) (0.5 μM dDssTP with respect to 10 μM natural base substrate). In the case not adding dDssTP (the lane shown as none in the electrophoresis photograph in FIG. 4), the replication stops just before Pa in the template DNA to show a band of 28-mer, which reveals that DNA strand extends depending on dDssTP. That is, it is revealed that dDssTP complements Pa of a template DNA and is thereby selectively incorporated into a complementary DNA strand.

Example 10

Incorporation of Unnatural Fluorescent Base Substrate into RNA by Transcription

As an example of incorporation of an unnatural fluorescent base substrate into RNA by transcription, an experiment of incorporation of ss or Dss into RNA by transcription using a T7 RNA polymerase was performed.

Templates for transcription by the T7 polymerase were prepared by heating chemically synthesized two DNA strands (10 μM coding strand (SEQ ID NO: 4) of 35-mer and non-coding strand (SEQ ID NO: 5) of 21-mer) at 95° C. in a 10 mM Tris-HCl buffer (pH 7.6) containing 10 mM NaCl and then slowly cooled to 4° C. for annealing. The transcription by the T7 polymerase was performed by using 2 μM of the template and 50 units of a T7 RNA polymerase (Takara Shuzo Co., Ltd., Kyoto) in a 40 mM Tris-HCl buffer (pH 8.0, 20 μL) containing 24 mM $MgCl_2$, 2 mM spermidine, 5 mM DTT, and 0.01% Triton X-100 in the presence of 1 mM natural NTPs, 0.05 to 0.1 mM ssTP or DssTP (ribonucleoside 5'-triphosphate of ss or Dss). After the reaction at 37° C. for 3 hr, the reaction was terminated by addition of a dye solution (20 μL) containing 10 M urea and 0.05% BPB. The solution mixture was heated at 75° C. for 3 min and was then subjected to electrophoresis with 20% polyacrylamide-7 M urea gel. The transcription product was protected by placing the gel on a TLC containing a fluorescent indicator, irradiating the gel with UV of 254 nm, and photographing the image with a Polaroid camera utilizing the phenomenon that nucleic acid absorbs the UV and thereby the band of the transcription product is detected as an image. The transcript including the unnatural fluorescent base ss or Dss was detected with a bio-imaging analyzer, LAS 4000 (Fujifilm Corporation) utilizing epi-UV LED. FIG. 4 shows the results.

Each of the unnatural base substrates, ssTP and DssTP, complemented Pa in the template DNA and was thereby incorporated into RNA. In FIG. 4B, the upper electrophoresis shows the incorporation of ssTP and the lower shows the incorporation of DssTP. In each electrophoresis, the left shows the detection by UV shadowing, and the right shows detection of fluorescence with LAS 4000 when excitation was performed with an epi-UV LED light source of which main wavelength is 365 nm. Accordingly, all RNA transcripts are detected as bands by the electrophoresis in the left, and RNA transcripts containing unnatural fluorescent bases are detected as bands by the electrophoresis in the right. As shown in FIG. 4B, the full length transcription product (17-mer (SEC ID NO: 6)) of each of ssTP and DssTP is recognized only when the template DNA incudes Pa. In the template DNA not including Pa (the lane in the left in each electrophoresis photograph), no fluorescent transcripts are detected. These reveals that each unnatural fluorescent base substrate is selectively incorporated into RNA depending on Pa.

Example 11

Unnatural Fluorescent Base Showing Properties as Universal Base

A nucleotide having Dss was introduced into the center of a 12-mer DNA, and a natural base was incorporated into the corresponding position of a strand complementary to the DNA. The thermal stability of the double-stranded DNA of each of the DNA strands was measured. The thermal stability of the double-stranded DNA containing Dss was measured with a Shimadzu UV-2450 spectrophotometer, and the Tm value was calculated by primary differentiation using Igor Pro software (WaveMetrics, Inc.). The change in temperature depending on the natural base was measured at an absorbance of 260 nm using 5 μM of each double-stranded DNA (length: 12 base pairs) in 100 mM sodium chloride, 10 mM sodium phosphate (pH 7.0), and 0.1 mM EDTA. FIG. 5 (left) shows the results.

The DNA fragment containing the unnatural fluorescent base Dss forms a double strand with each complementary DNA, and the thermal stability of each double-stranded DNA is substantially the same in every base pair formed between Dss and any natural base (Tm=43.9 to 45.9° C.). The thermal stability of these double-stranded DNAs is lower than that of an A-T base pair ($T_m$=48.6° C.) by only 3° C., but is higher than that of a T-G base pair ($T_m$=42.4° C.), which is the most stable mismatched base pair in natural bases.

In 3-nitropyrrole, which is frequently used as a known universal base, the stability of double-stranded DNA is considerably reduced compared to that of a natural base pair, and the thermal stability (Tm) ranged from 17.8° C. to 23.2° C. depending on the complementary natural base (FIG. 5, right).

Thus, Dss does not largely reduce the stability of double-stranded DNA and does not cause a large change in thermal stability caused by difference of the complementary natural base. Accordingly, Dss is superior to known base analogs, as a universal base.

Example 12

Preparation of shRNA Site-Specifically Containing Unnatural Fluorescent Base Dss or ss In this Example, 52-mer shRNA (shRNAF1) containing an unnatural fluorescent base (Dss or ss) was prepared through transcription by T7 RNA polymerase utilizing an unnatural base pair Dss-Pa or ss-Pa. The shRNAF1 (SEQ ID NO: 10) is a shRNA (short hairpin RNA) for RNA interference experiment using mRNA of firefly luciferase as a target. FIG. 6A shows a secondary structure of shRNAF1. The unnatural fluorescent base, Dss or ss, is introduced at the 10th, 12th, 16th, 20th, or 21st position in the passenger strand of a transcription product and at any of the 34th to 41st position in the guide strand. The shRNA product containing the unnatural base was identified based on difference between the mobility in electrophoresis of the shRNA product containing the unnatural base and that of a product into which the unnatural fluorescent base is not incorporated, and by detecting the fluorence of the band corresponding to the shRNA product containing the unnatural base by UV (wavelength: 365 nm) irradiation.

(1) Preparation of Template for T7 Transcription

For RNA interference experiment which targets mRNA of firefly luciferase, DNA templates for transcribing shRNA (shRNAF1, full length: 52-mer) containing an unnatural fluorescent base, Dss or ss, at specific positions were prepared, by heating chemically synthesized two DNA strands (667 nM coding strand and non-coding strand each of 69-mer) containing Pa at 95° C. in a 10 mM NaCl-10 mM Tris-HCl buffer (pH 7.6) and then slowly cooling them to 4° C. for annealing.

(2) T7 Transcription

T7 transcription was performed by using an Ampliscribe T7-Flash Transcription Kit from Epicentre Biotechnologies Inc. in the presence of 200 nM of template DNA, 2 mM of natural NTPs, and 0.1 mM of DssTP or 0.1 mM of ssTP at 37° C. for 2 hr. The solution after the reaction was desalted to replace with a TE buffer by using Micro-conYM-3 (Millipore Corporation), and the target full-length shRNA was purified by electrophoresis with 15% polyacrylamide-7 M urea gel.

Example 13

Figure 6:
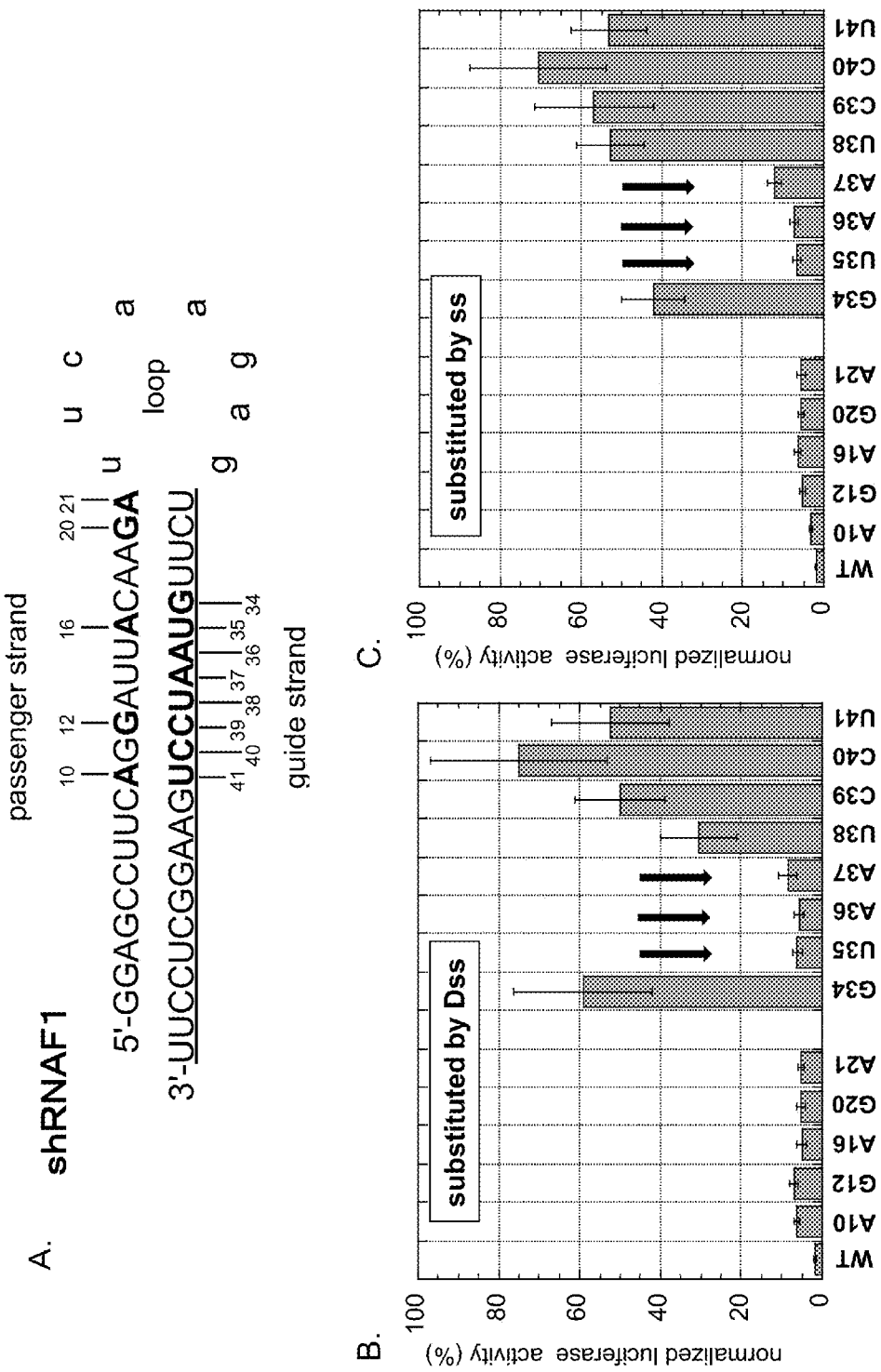
FIG. 6 illustrates the results of the effects of several shRNAF1 mutants on suppressing expression of a firefly luciferase gene, A: a diagram illustrating the structure of shRNAF1, B: a graph illustrating the results of the effects of shRNAF1 mutants having unnatural base Dss substitution on suppressing expression of a firefly luciferase gene, and C: a graph illustrating the results of the effects of shRNAF1 mutants having unnatural base ss substitution on suppressing expression of a firefly luciferase gene.

Introduction of each shRNA Mutant into Cultured Cells and Analysis of Effect of Suppressing Reporter Gene Expression In this Example, various shRNAs prepared by T7 transcription and gel purification were introduced into HeLa cells by lipofection together with a plasmid encoding a target reporter gene (firefly luciferase) and a control plasmid endocing a *Renilla* luciferase gene. Suppression of the target gene expression was investigated based on the luminescence of luciferase. FIG. 6 shows the results.

(1) Cell Culture

HeLa cells were cultured under conditions of a carbon dioxide concentration of 5% and an incubation temperature of 37° C. in an MEM medium (Minimum Essential Medium Eagle, Sigma-Aldrich Corporation) containing 10% fetal bovine serum (FBS, JRH Biosciences, Inc.) and supplemented with antibiotics (100 U/mL of a final concentration of penicillin, and 100 µg/mL of streptomycin).

(2) Introduction of shRNA and Plasmids into Cells

HeLa cells were seeded at $1.5 \times 10^4$ cells (100 µL of culture medium)/well in a 96-well plate and were cultured in an MEM medium containing 10% fetal bovine serum but not containing antibiotics for 24 hr. Transfection was performed by addition of a solution (50 µL) including a Lipofectamine 2000 reagent (Invitrogen Corporation, 0.5 µL/well), a plasmid encoding a firefly luciferase gene (pGL3-control manufactured by Promega Corporation, 200 ng/well), a plasmid encoding a *Renilla* luciferase gene (pGL4.74[ hRluc/TK] manufactured by Promega Corporation, 200 ng/well), and any of shRNAs annealed in PBS (75 fmol/well) in an OPTI-MEM medium (Invitrogen Corporation). The final concentration of the shRNA in tranfection was 0.5 nM. After culturing for 22 hr, the intensity of luminescence emitted from each of the two types of luciferase proteins was determined.

(3) shRNA Effects on Suppressing Reporter Gene Expression

The effect of suppressing expression of the firefly luciferase protein, which is the target of shRNA, was analyzed by the intensities of luminescence emitted from the firefly luciferase and *Renilla* luciferase using dual luciferase reporter assay reagent (Promega Corporation). Specifically, the cells after transfection were washed with 100 µL per well of PBS twice and were then lysed with 20 µL of a cytolysis buffer with gently stirring at 25° C. for 30 min. The resulting solution was mixed with 100 µL of LAR II reagent, and the luminescence of the firefly luciferase was detected (exposure time: 120 sec) with LAS 4000 (Fujifilm Corporation), then, 100 µL of Stop & Glo reagent was added thereto, and the luminescence of the *Renilla* luciferase was detected (exposure time: 200 sec). The intensity of each luminescence was quantitatively measured with Science Lab 2005 Multi Gauge (Fujifilm Corporation). In each detection, the intensity of luminescence when the transfection was not performed was used as the background. The background was subtracted from the intensity of luminescence of each luciferase, and the intensity of luminescence of the firefly luciferase as the target was divided by the intensity of luminescence of the *Renilla* luciferase coexpressed as the control for normalization. The relative activity of the firefly luciferase as the target in the presence of various types of shRNAs was calculated using the value in the absence of shRNA as 100%.

In comparison with the activity of shRNAF1 (WT), the substitution of the 10th, 12th, 16th, 20th, or 21st base in the passenger strand of shRNA with an unnatural fluorescent base hardly affected the activity of the shRNA mutant as in the substitution with a natural base. In the substitution of any of the 34th to 41st bases in the guide strand with unnatural fluorescent bases, only the substitution of the 35th, 36th, or 37th base allowed introduction of the unnatural fluorescent base with maintaining the shRNA activity. The amount of IFN-α secreted in the medium after transfection of the shRNA at a final concentration of 0.5 nM was 80 µg/mL or less in every case. Thus, significant induction of IFN-α by introduction of the shRNA was not recognized.

The results reveal that substitution by unnatural bases Dss or ss can be available not only within the passenger strand but also in some position within the guide strand, without affecting the activity of shRNA.

Example 14

Figure 7:
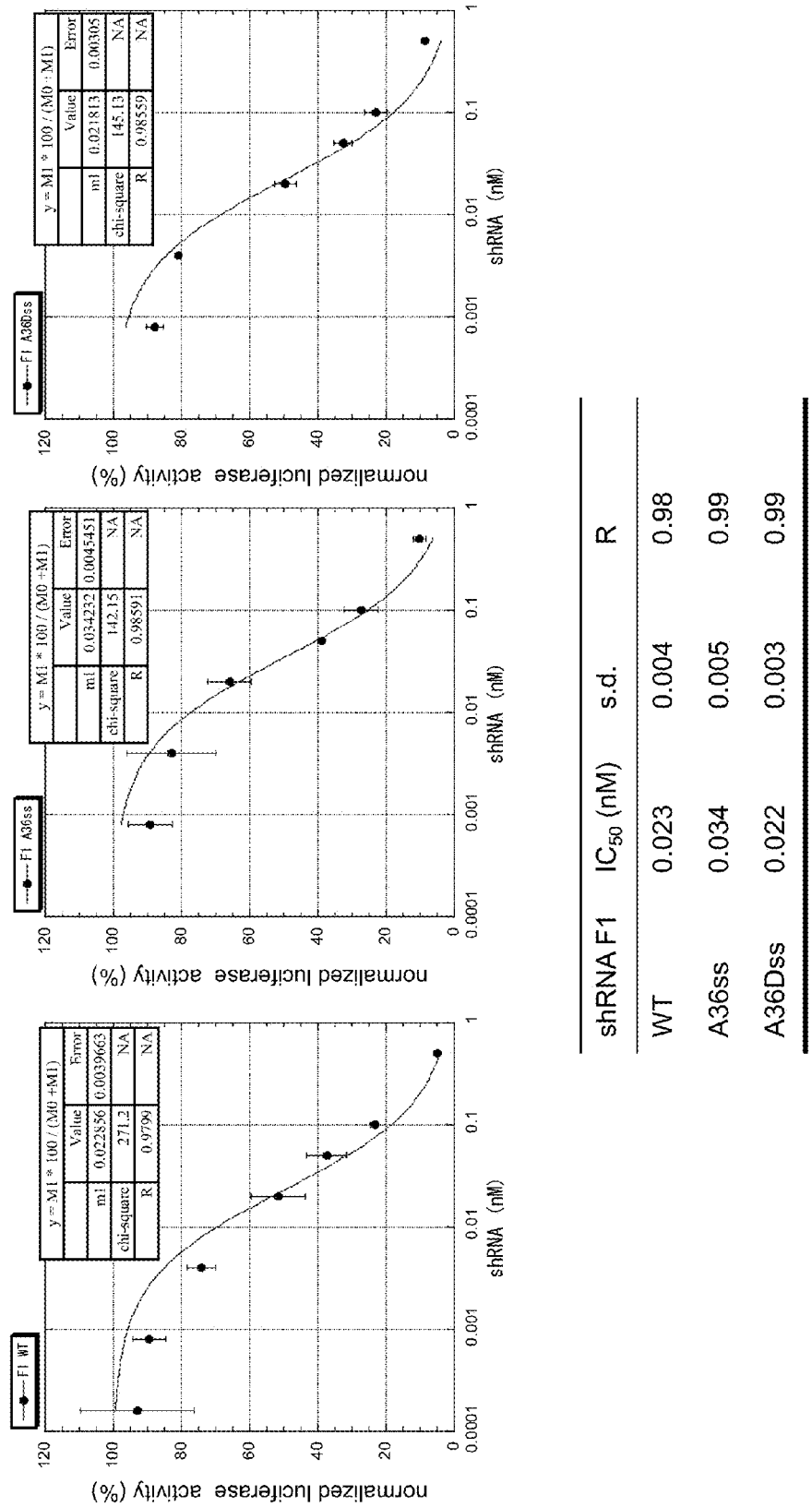
FIG. 7 includes graphs (upper) illustrating a calculation process of $IC_{50}$ for the effects of shRNAF1 mutants (A36 substitution) on suppressing expression of a firefly luciferase gene and a table (lower) illustrating $IC_{50}$ values.

Effect of Various shRNAs on Suppressing Expression of Reporter Gene—Calculation of $IC_{50}$ To calculate $IC_{50}$ of shRNA variants containing the unnatural base, Dss or ss, at the 36th base, and shRNA F1 WT, suppression of gene expression was analyzed at different concentrations of each shRNA. The $IC_{50}$ value was calculated with Kaleidagraph software (Albeck Software) thorugh curve ftting to the following equation: $y=100 \times M1/(M0+M1)$ by a least-squares method, where y (%) corresponds to the relative activity (see Example 2) of luciferase as a target in the presence of shRNA, M0 (nM) corresponds to the shRNA concentration, and $IC_{50}$ value corresponds to M1 (nM). FIG. 7 shows the results. The $IC_{50}$ value of shRNAF1 where A36 was substituted with Dss or ss was about 0.02 nM, which was similar to that of shRNAF1 WT where A36 was unsubstituted.

Example 15

Observation of Fluorescence of shRNA Containing Unnatural Fluorescent Base

The unnatural base Dss or ss introduced into shRNA can emit blue fluorescence by excitation with UV at a longer wavelength side. Accordingly, detection of shRNA using the fluorescence of the unnatural base Dss or ss was compared with that using the known unnatural fluorescent base s.

As the shRNA, shRNAF1 U35Dss where U35 of shRNAF1 was substituted with Dss, shRNAF1 U35ss where U35 of shRNAF1 was substituted with ss, and shRNAF1 U35s where U35 of shRNAF1 was substituted with s, were used.

Figure 8:
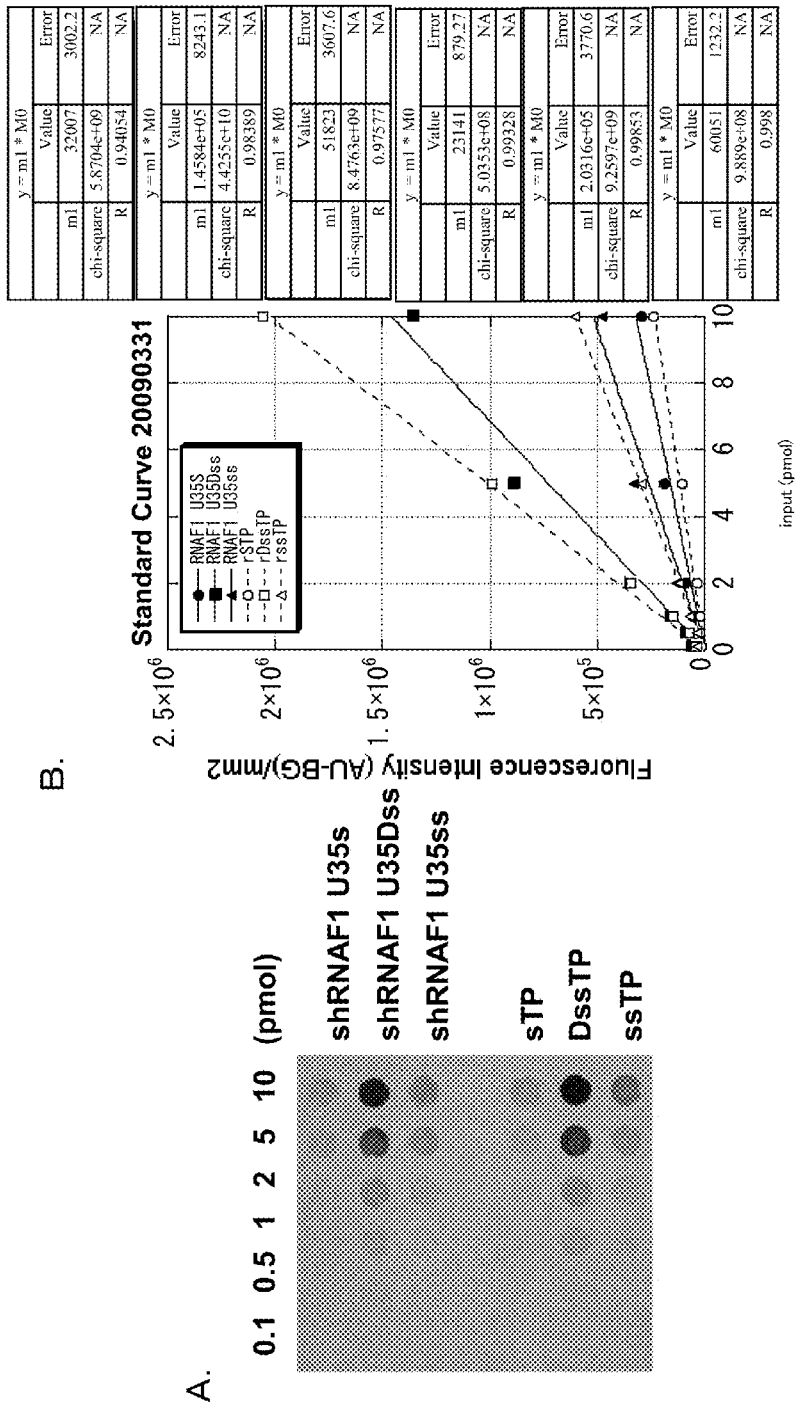
FIG. 8 includes a photograph (A) and a graph (B) illustrating the observed results of fluorescence of shRNAF1 mutants (U35 substitution) and ribonucleoside 5'-triphosphate on a nylon membrane.
Figure 9:
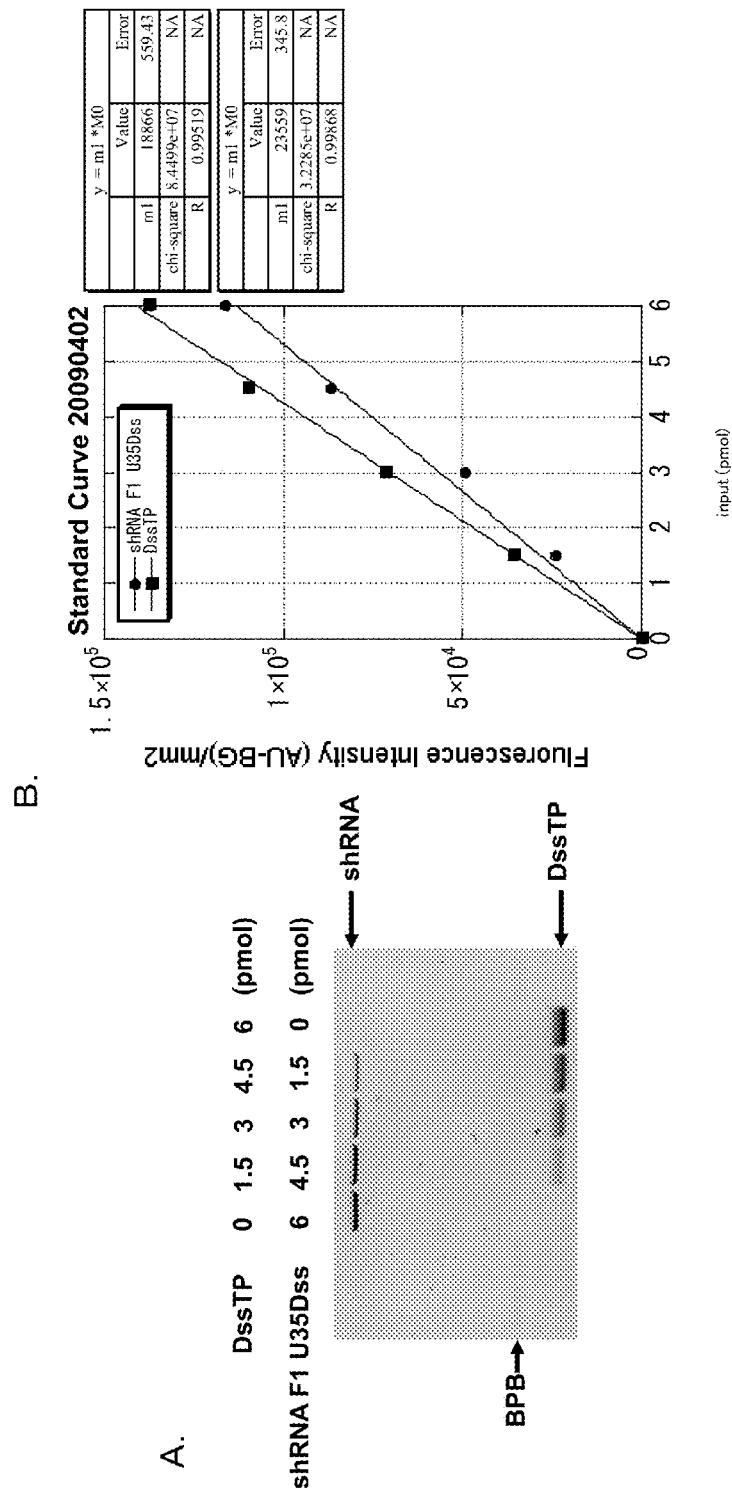
FIG. 9 includes a photograph (A) and a graph (B) illustrating separation of a shRNAF1 mutant (U35 substitution) and ribonucleoside 5'-triphosphate by electrophoresis and the results of fluorescence observation thereof. The graph shows plots of fluorescence intensity of a band on the gel versus the loaded amount.

A predetermined amount of each shRNA was dot-blotted to a nylon membrane with a 96-well manifold, and then the fluorescence thereof was detected by a DAPI mode (epi-UV LED light source, main wavelength: 365 nm, detection filter L41) of a bio-imaging analyzer LAS 4000 (Fujifilm Corporation). FIG. 8 shows the results. The maximum wavelengths of fluorescence of sTP, ssTP, and DssTP excited with light of 365 nm were 436 nm, 468 nm, and 459 nm, respectively. The fluorescence intensities at these wavelengths were DssTP>ssTP>sTP. The sensitivities of detecting shRNA were also U35Dss>U35ss>U35s. Furthermore, the fluorescence intensity was proportional to the amount of shRNA (graph of FIG. 8B). In addition, the substrates and shRNAs of these unnatural fluorescent bases were quantitatively detected on polyacrylamide gel (FIG. 9). Accordingly, the fluorescence intensities of Dss and ss each show a linear relationship with the concentration thereof, which allows quantitative measurement of shRNAs and identification or investigation of a degradation process of shRNA from the respective fluorescence intensities. It was revealed that the sensitivities of both Dss and ss are high compared to the known unnatural fluorescent base s, in particular, the sensitivity of Dss is notably high under the conditions of this Example.

Example 16

Figure 10:
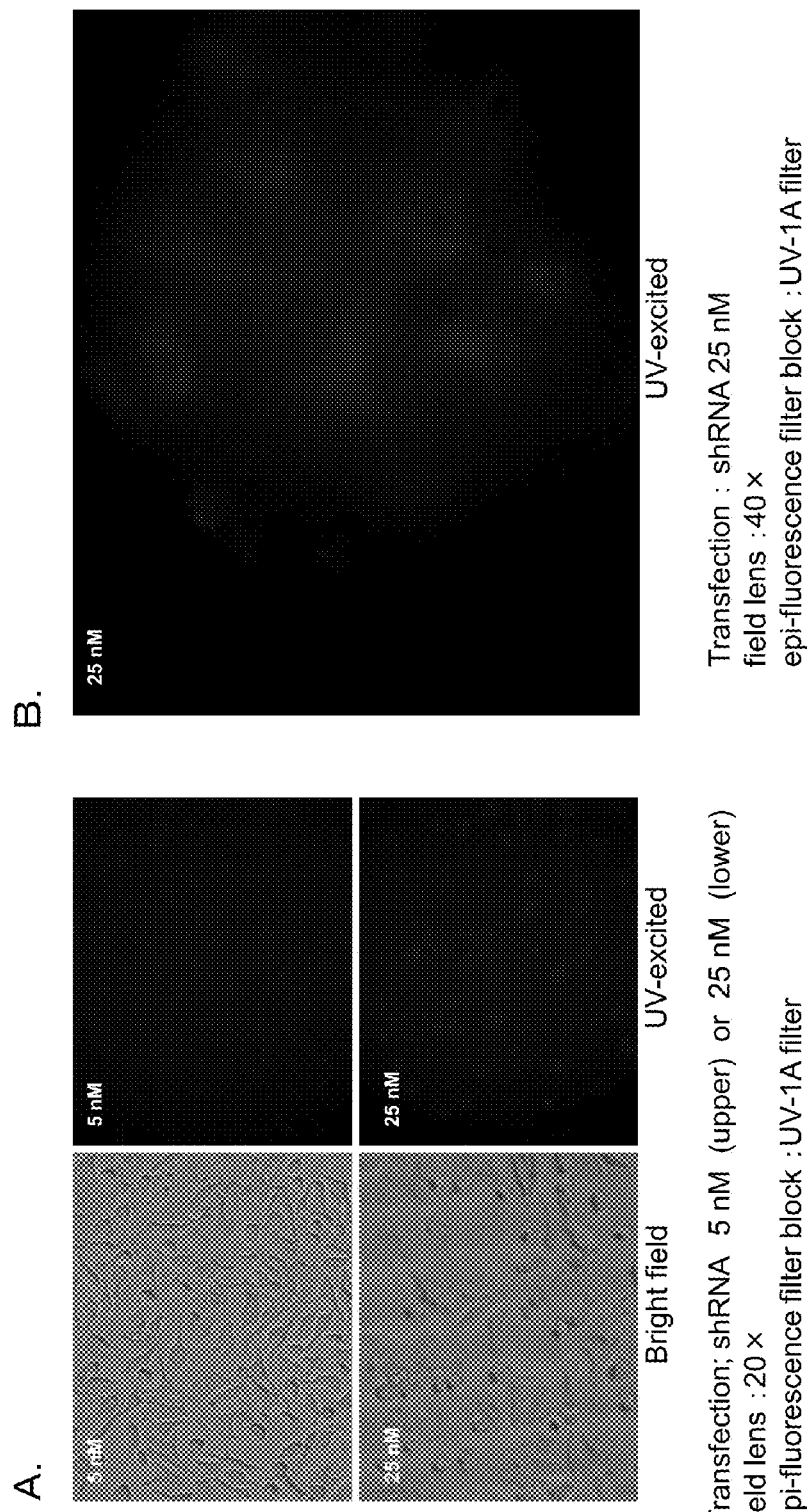
FIG. 10 includes photographs of cells 20 hr after transfection with a shRNAF1 A36Dss mutant, A: photographs (magnification: 20 times) illustrating the observed results at a bright field (left) and the observed results under UV excitation (right) when cells are transfected with 5 nM (upper) or 25 nM (lower) of shRNA, and B: a photograph (magnification: 40 times) illustrating the observed results under UV excitation when cells are transfected with 25 nM of shRNA.

Observation of Fluorescence of shRNA Containing Unnatural Fluorescent Base in Cells HeLa cells were transfected with 5 nM or 25 nM of shRNAF1 A36Dss where the A36 of shRNAF1 was substituted with Dss and were incubated for 20 hr. The medium was replaced by PBS, and the cells were observed with a fluorescence microscope (Nikon Eclipse-Ti, inverted fluorescence microscope, epi-fluorescence filter block UV-1A filter). FIG. 10 shows the fluorescence microscopic photographs showing the results. The fluorescence observed by UV excitation overlaps with the cells observed at a bright field to show that the fluorescence was that from the Dss contained in shRNA that was introduced into the cells by transfection. This experiment revealed that fluorescence in cells transfected with several tens of nanomoles of shRNA can be observed.

The results of Examples 12 to 16 demonstrate that the unnatural fluorescent base of the present invention can be introduced into functional RNA by transcription, that the activity of the functional RNA is maintained, and that the functional RNA is labeled with fluorescence.

INDUSTRIAL APPLICABILITY

The unnatural bases and unnatural base pair technology of the present invention can be applied to various basic and applied researches such as site-specific labeling of DNA or RNA with fluorescence, analysis of local structure of nucleic acid conformation, fluorescence labeling and dynamic analysis of nucleic acid drugs, real time PCR, and SNP analysis.

SEQUENCE LIST FREE TEXT

SEQ ID NO: 1: template for DNA replication
SEQ ID NO: 2: primer for DNA replication
SEQ ID NO: 3: replicated DNA
SEQ ID NO: 4: template DNA for T7 transcription
SEQ ID NO: 5: primer for T7 transcription
SEQ ID NO: 6: transcribed RNA
SEQ ID NO: 7: DNA for thermal stability test
SEQ ID NO: 8: DNA for thermal stability test
SEQ ID NO: 9: DNA for thermal stability test
SEQ ID NO: 10: shRNA of which target is firefly luciferase mRNA

---

The invention claimed is:

1. A compound comprising an unnatural base represented by Formula I:

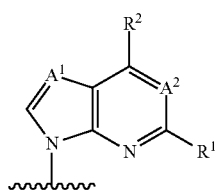

wherein, $A^1$ represents N or CH;

$A^2$ represents CH;

$R^1$ represents hydrogen or an amino group; and $R^2$ represents a substituent selected from the group consisting of a 2,2'-bithien-5-yl group, a 2-(2-thiazolyl)thien-5-yl group, a 5-(2-thienyl)thiazol-2-yl group, and a 2,2',5',2''-terthien-5-yl group;

or a derivative wherein an amino group in the unnatural base is protected by a protecting group of a phenoxyacetyl group, an isobutyryl group, or a dimethyl formamidyl group;

or a derivative thereof wherein the thienyl group or the thiazolyl group contained in $R^2$ is further substituted with a methyl group, an amino group, a hydroxyl group, or a thiol group.

2. The compound according to claim 1, represented by Formula II:

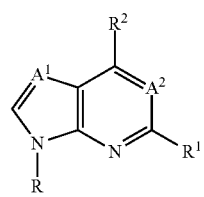

wherein,
A¹ represents N or CH;
A² represents CH;
R is selected from the group consisting of hydrogen, a methyl group, carbohydrates, ribose, and deoxyribose;
R¹ represents hydrogen or an amino group; and
R² represents a substituent selected from the group consisting of a 2,2'-bithien-5-yl group, a 2-(2-thiazolyl)thien-5-yl group, a 5-(2-thienyl)thiazol-2-yl group, and a 2,2',5',2''-terthien-5-yl group.

3. The compound according to claim 1, comprising a group selected from the group consisting of:
(i) a 7-(2,2'-bithien-5-yl)imidazo[4,5-b]pyridin-3-yl group (Dss);
(ii) a 7-(2,2',5',2''-terthien-5-yl)imidazo[4,5-b]pyridin-3-yl group (Dsss);
(iii) a 4-(2,2'-bithien-5-yl)-pyrrolo[2,3-b]pyridin-1-yl group (Dsas);
(iv) a 4-[2-(2-thiazolyl)thien-5-yl]pyrrolo[2,3-b]pyridin-1-yl group (Dsav); and
(v) a 4-[5-(2-thienyl)thiazol-2-yl]pyrrolo[2,3-b]pyridin-1-yl group (Dvas).

4. A nucleoside or nucleotide or a phosphoramidite derivative thereof or a H-phosphonate derivative thereof, comprising an unnatural base represented by Formula I:

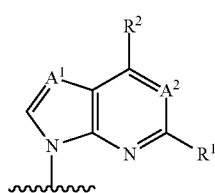

(I)

wherein,
A¹ represents N or CH;
A² represents CH;
R¹ represents hydrogen or an amino group; and
R² represents a substituent selected from the group consisting of a 2,2'-bithien-5-yl group, a 2-(2-thiazolyl)thien-5-yl group, a 5-(2-thienyl)thiazol-2-yl group, and a 2,2',5',2''-terthien-5-yl group.

5. The nucleoside or nucleotide or the derivative thereof according to claim 4, wherein the unnatural base represented by Formula I is selected from the group consisting of:
(i) a 2-amino-6-(2,2'-bithien-5-yl)purin-9-yl group (ss); and
(ii) a 2-amino-6-(2,2',5',2''-terthien-5-yl)purin-9-yl group (sss).

6. The nucleoside or nucleotide or the derivative thereof according to claim 4, wherein the nucleoside or the nucleotide comprises β-D-ribofuranosyl or 2-deoxy-β-D-ribofuranosyl as a carbohydrate moiety.

7. The nucleoside or nucleotide or the derivative thereof according to claim 4, wherein the nucleotide is deoxyribonucleoside 5'-triphosphate or ribonucleoside 5'-triphosphate.

8. The nucleoside or nucleotide or the derivative thereof according to claim 4, being a phosphoramidite derivative.

9. The nucleoside or nucleotide or the derivative thereof according to claim 4, emitting fluorescence by excitation at a wavelength of 200 nm or more.

10. The nucleoside or nucleotide or the derivative thereof according to claim 4, being used as a universal base.

11. A nucleic acid containing a nucleotide according to claim 4.

12. The nucleic acid according to claim 11, emitting fluorescence by excitation at a wavelength of 200 nm or more.

13. The nucleic acid according to claim 11, being a functional nucleic acid selected from the group consisting of antisense DNAs, antisense RNAs, ribozymes, deoxyribozymes, RNA interference-inducing nucleic acids such as siRNAs and shRNAs, microRNAs, anti-microRNA nucleic acid molecules, decoy nucleic acids, DNA aptamers, and RNA aptamers.

14. The nucleic acid according to claim 11, being an amplification primer that is used in a nucleic acid amplification process selected from the group consisting of LAMP method, SDA method, SMAP method, NASBA method, ICAN method, UCAN method, TMA method, Padlock Probe method, RCA method, bDNA method, PALSAR method, Invader method, TRC method, CPT method, and Plexor method.

15. The nucleic acid according to claim 11, being a target nucleic acid detecting probe selected from the group consisting of molecular beacons, Taqman probes, Scorpion-based probes, and Riboswitches.

16. A nucleic acid mimic comprising:
a base moiety comprising an unnatural base represented by Formula I:

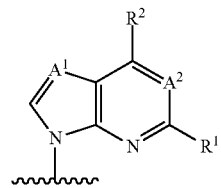

(I)

wherein,

A¹ represents N or CH;

A² represents CH;

R¹ represents hydrogen or an amino group; and

R² represents a substituent selected from the group consisting of a 2,2'-bithien-5-yl group, a 2-(2-thiazolyl)thien-5-yl group, a 5-(2-thienyl)thiazol-2-yl group, and a 2,2',5',2''-terthien-5-yl group or a derivative thereof wherein an amino group in the unnatural base is protected by a protecting group of a phenoxyacetyl group, an isobutyryl group, or a dimethyl formamidyl group;

or a derivative thereof wherein the thienyl group or the thiazolyvl group contained in R² is further substituted with a methyl group, an amino group, a hydroxyl group, or a thiol group; and a backbone moiety being a nucleic acid mimic backbone selected from the group consisting of morpholinonucleotides, locked nucleic acids (LNAs), and peptide nucleic acids (PNAs).

17. A method of introducing an unnatural base represented by Formula I into a DNA or RNA:

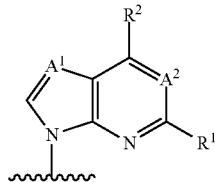

(I)

wherein,
$A^1$ represents N or CH;
$A^2$ represents CH;
$R^1$ represents hydrogen or an amino group; and
$R^2$ represents a substituent selected from the group consisting of a 2,2'-bithien-5-yl group, a 2-(2-thiazolyl)thien-5-yl group, a 5-(2-thienyl)thiazol-2-yl group, and a 2,2',5',2''-terthien-5-yl group or a derivative thereof wherein an amino group in the unnatural base is protected by a protecting group of a phenoxyacetyl group, an isobutyryl group, or a dimethyl formamidyl group;

or a derivative thereof wherein the thienyl group or the thiazolyl group contained in $R^2$ is further substituted with a methyl group, an amino group, a hydroxyl group, or a thiol group into DNA or RNA by replication of a nucleic acid, wherein said method comprises using a template strand which is a nucleic acid containing a nucleotide having a base represented by Formula III:

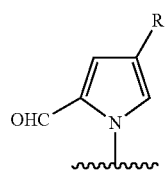

(III)

wherein,
R is selected from the group consisting of hydrogen and substituted or unsubstituted alkyl, alkenyl, and alkynyl groups, wherein the substituted alkyl, alkenyl, or alkynyl group is substituted with a functional group or a fluorescent functional group;

conducting replication, transcription, or reverse transcription of a nucleic acid by using deoxyribonucleoside 5'-triphosphate or ribonucleoside 5'-triphosphate having an unnatural base represented by Formula I as a replication substrate;

thereby producing a nucleic acid containing a base pair of the base represented by Formula III and the unnatural base represented by Formula I and a nucleotide having the unnatural base represented by Formula I is introduced into DNA or RNA.

18. A method of introducing an unnatural base represented by Formula I into a DNA or RNA:

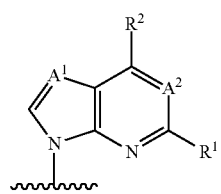

(I)

wherein,
$A^1$ represents N or CH;
$A^2$ represents CH:
$R^1$ represents hydrogen or an amino group; and
$R^2$ represents a substituent selected from the group consisting of a 2,2'-bithien-5-yl group, a 2-(2-thiazolyl)thien-5-yl group, a 5-(2-thienyl)thiazol-2-yl group, and a 2,2',5',2''-terthien-5-yl group or a derivative thereof wherein an amino group in the unnatural base is protected by a protecting group of a phenoxyacetyl group, an isobutyryl group, or a dimethyl formamidyl group;

or a derivative thereof wherein the thienyl group or the thiazoly group contained in $R^2$ is further substituted with a methyl group, an amino group, a hydroxyl group, or a thiol group into DNA or RNA by chemical synthesis, wherein said method comprises synthesizing the DNA or RNA incorporating a phosphoramidite derivative of a nucleoside having an unnatural base represented by Formula I into a DNA or RNA.

* * * * *